(12) United States Patent
Hama et al.

(10) Patent No.: US 7,433,115 B2
(45) Date of Patent: Oct. 7, 2008

(54) LIGHT EMITTING DEVICE

(75) Inventors: Atsutomo Hama, Anan (JP); Shinichi Nagahama, Anan (JP); Yukihiro Hayashi, Anan (JP)

(73) Assignee: Nichia Corporation, Anan-shi (JP)

( * ) Notice: Subject to any disclaimer, the term of this patent is extended or adjusted under 35 U.S.C. 154(b) by 331 days.

(21) Appl. No.: 11/302,469

(22) Filed: Dec. 14, 2005

(65) Prior Publication Data
US 2006/0152926 A1 Jul. 13, 2006

(30) Foreign Application Priority Data

Dec. 15, 2004 (JP) .............................. 2004-363103
Dec. 17, 2004 (JP) .............................. 2004-366646

(51) Int. Cl.
*G02F 2/02* (2006.01)
*H01S 3/10* (2006.01)

(52) U.S. Cl. .............................. 359/326; 372/21; 385/28

(58) Field of Classification Search ................. 359/326, 359/328; 385/28, 29; 372/6, 21
See application file for complete search history.

(56) References Cited

U.S. PATENT DOCUMENTS

| | | | | |
|---|---|---|---|---|
| 5,054,878 A | * | 10/1991 | Gergely et al. ................. | 385/33 |
| 6,717,355 B2 | * | 4/2004 | Takahashi et al. ........... | 313/503 |
| 6,724,522 B2 | * | 4/2004 | Hartung ....................... | 359/332 |
| 7,277,618 B2 | * | 10/2007 | Yamazaki et al. ........... | 385/123 |
| 2005/0215861 A1 | | 9/2005 | Hakamata | |

FOREIGN PATENT DOCUMENTS

WO    WO01/40702 A1    6/2001

* cited by examiner

*Primary Examiner*—Hemang Sanghavi
(74) *Attorney, Agent, or Firm*—Global IP Counselors, LLP

(57) ABSTRACT

A light emitting device comprises a first unit and a second unit, the first unit comprising: a first excitation light source comprising a laser element emitting blue wavelength band excitation light; a first wavelength converting member comprising at least one type of fluorescent material and which absorbs at least a portion of a first excitation light emitted from the first excitation light source, converts the wavelength, and releases light with a wavelength longer than the first excitation light; and a first light guide which has a refractive index in the center region of the cross-section which is higher than the refractive index of the surrounding region and which transmits the first excitation light emitted from the first excitation light source; and the second unit comprising: a second excitation light source comprising a laser element which emits excitation light with a wavelength band shorter than the blue wavelength band excitation light emitted by the laser element; a second wavelength converting member which is similar of the above; and a second light guide which is similar of the above.

26 Claims, 13 Drawing Sheets (a)

(b)

(a) LD(445nm) + LAG + SCESN (b) LD(405nm) + CCA + LAG + SCESN (c) LD(445nm) + LD(405nm)

LIGHT EMITTING DEVICE

BACKGROUND OF THE INVENTION

1. Field of the Invention

The present invention relates to a light emitting device, and more particularly relates to light emitting device which has an excitation light source, a wavelength converting member, and a light guide.

2. Background Information

Conventionally, endoscope devices for in vivo observations and for performing treatment during observations, and fiber scopes for observing in extremely narrow or extremely dark spaces have been widely used.

Endoscopes and fiber scopes are constructed with extremely minute light guides and are able to illuminate spaces or the like such as inside body cavities like the stomach or other gaps or the like because the fibers transfer light which has been radiated from a light source.

In order to efficiently illuminate using minute fibers, the light source must be very bright. Furthermore, when observing and in some cases diagnosing an affected area of an organ or within cavities, accurate reproduction of color information is necessary. Thus, the light source for endoscopes and fiber scopes must provide light which is close to natural light.

Therefore, the use of semiconductor light emitting elements such as light emitting diode elements (LED) and laser diode elements (LD) or the like have been proposed as light sources to replace xenon lamps or the like (for instance, JP 2002-95634-A).

Furthermore, an illuminating device which uses semiconductor light emitting elements has been proposed (for instance, JP 2003-515899-A).

Semiconductor light emitting elements are compact, have good power efficiency, and emit brilliant colored light. Furthermore, these elements are formed from semiconductors, so there is no concern that the elements will burn out. In particular, semiconductor lasers emit light which has extremely high intensity compared to that of light emitting diodes, and therefore can realize light sources with excellent illumination.

In recent years, semiconductor lasers which emit blue wavelength light have been developed, and the light emitting efficiency thereof is extremely high. Therefore, various illuminating devices and light emitting devices which use semiconductor lasers as light sources for achieving RGB light have been proposed. These devices have been able to overcome conventional issues, such as failure to achieve sufficient light emitting efficiency and brightness, by using wavelength converting members which emit blue light.

However, as described above, when using an endoscope or the like, a device with excellent color rendering properties is required. Furthermore, excellent color rendering properties are also required of illuminating devices for automotive applications in order to distinguish people and signs.

In particular, sufficient color rendering properties cannot be sufficiently achieved when using a semiconductor laser which emits blue wavelength light because of the unique properties of this laser, namely the property of having a linear spectrum in the blue wavelength band and having extremely low light emitting intensity across a relatively wide band of adjacent wavelength bands (such as near ultraviolet bands and blue-green wavelength bands).

In addition, extremely high brightness may be required depending on the use of the light source device, but there is a mutual trade-off relationship between light emitting efficiency/brightness and color rendering properties, and sufficiently achieving satisfactory levels of both light emitting efficiency and color rendering properties is difficult.

Note that semiconductor light emitting elements such as semiconductor lasers are required to have even higher brightness and high light emitting efficiency, but the light density is generally high, so the resins and the fluorescent material or the like which make up the wavelength converting member will be heated and degraded by the high density excitation light, thus leading to a shorter life for the light emitting device.

SUMMARY OF THE INVENTION

An object of the present invention is to provide a light emitting device which can achieve excellent color rendering properties for color reproduction using a semiconductor laser which emits blue wavelength light with good light emitting efficiency and which has a linear spectrum in the blue wavelength band.

Furthermore, from another viewpoint, a further object is to provide a high-performance light emitting device which satisfies both properties of the mutual trade-off relationship between high color rendering properties and good light emitting efficiency which emits light at extremely high brightness.

Furthermore, from yet another viewpoint, another object is to prevent degradation of the materials which form the light emitting device using semiconductor light emitting elements with good light emitting efficiency, and to provide a light emitting device with long life.

The present invention provides a light emitting device comprising a first unit and a second unit, the first unit comprising: a first excitation light source which includes a laser element emitting blue wavelength band excitation light; a first wavelength converting member which includes at least one type of fluorescent material and which absorbs at least a portion of a first excitation light emitted from the first excitation light source, converts the wavelength, and releases light with a wavelength longer than the first excitation light; and a first light guide which has a refractive index in the center region of the cross-section which is higher than the refractive index of the surrounding region and which transmits the first excitation light emitted from the first excitation light source; and the second unit comprising a second excitation light source which includes a laser element which emits excitation light with a wavelength band shorter than the blue wavelength band excitation light emitted by the laser element; a second wavelength converting member which includes at least one type of fluorescent material and which absorbs at least a portion of a second excitation light emitted from the second excitation light source, converts the wavelength, and releases light with a wavelength longer than the second excitation light; and a second light guide which has a refractive index in the center region of the cross-section which is higher than the refractive index of the surrounding region and which transmits the second excitation light emitted from the second excitation light source.

Further, the present invention provides a light emitting device comprising:

a third excitation light source which emits third excitation light;

a third wavelength converting member which absorbs at least a part of the third excitation light emitted from the third excitation light source, converts the wavelength, and releases light with a predetermined wavelength band;

a third light guide with the third excitation light source at one end and the third wavelength converting member at the other end, and which has a refractive index in the center region of the cross-section which is higher than the refractive index of the surrounding region, and which transmits excitation light emitted from the third excitation light source to the third wavelength converting member; and a mode scrambler which applies mode scrambling to the third excitation light which is introduced to the third light guide.

Using the light emitting device of the present invention, excellent color rendering properties can be shown by using a combination of a laser elements which radiate very bright excitation light in the blue wavelength band together with another laser element.

Furthermore, using the light emitting device of the present invention, light which locally has high relatively intensity within the excitation light is neutralized by light with broad relative intensity, while essentially sustaining a high level of brightness for all of the excitation light which is radiated onto the wavelength converting member, by using a mode scrambler. Therefore, degradation caused by heating of the wavelength converting member due to high-intensity light can be prevented in order to improve reliability and obtain a light emitting device with long life.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1:
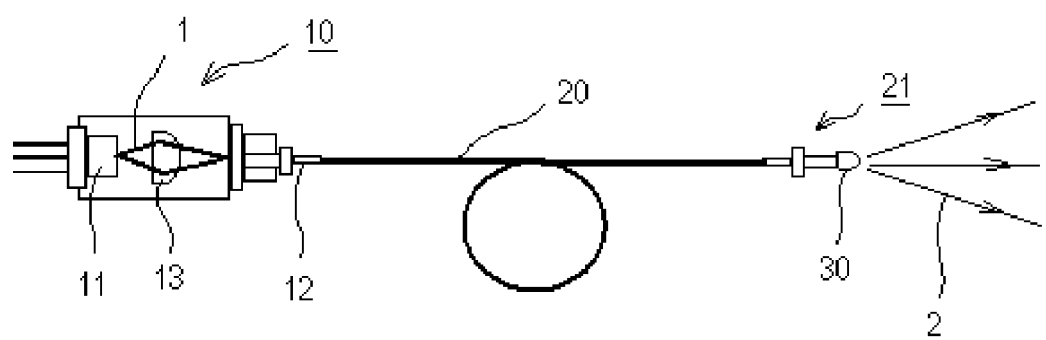
FIG. 1 is a schematic diagram for describing the unit structure of the light emitting device of the present invention.

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

The light emitting device of the present invention is able to simultaneously achieve both properties of the trade-off relationship between high light emitting efficiency and good color rendering properties.

Furthermore, by using laser elements as the excitation light source, the color temperature and the color coordinates will not easily change and the white intensity can be adjusted without changing the input power.

When a laser element which radiates excitation light with wavelengths in the 430 to 500 nm range is combined with a laser element which radiates excitation light with wavelengths in the 360 to 420 nm range, or when specific fluorescent material in a first unit and/or a second unit are used in combination, the effect of achieving good color rendering properties along with high brightness can be more positively achieved.

If a mode scrambler changes the radiation pattern of the excitation light guided by the light guide to a different radiation pattern and then radiates the excitation light from the light guide, degradation of the wavelength changing material because of heating can be more positively prevented.

If the mode scrambler is formed as a member with a concave region and/or a convex region facing a part or all of the outer circumference in part or all of the longitudinal direction of the light guide, the mode scrambler will bend the light guide in multiple directions or can be integrated to the light guide so that the diameter of the center region is changed by increasing or decreasing the thickness of the circumference of the light guide, and therefore the mode scrambler can be very easily achieved, and a high-performance device can be provided at a very low cost.

If the mode scrambler doubles or more than doubles the full width at half maximum value for the FFP of the excitation light radiated from the light guide, or reduces the intensity peak value to 80% or less for the FFP of the excitation light radiated from the light guide, heating of the wavelength changing material can be better prevented, and a high-performance light emitting device with longer life can be achieved.

The wavelength converting member comprises fluorescent material and resin, and when the fluorescent material and resin are mixed in a weight ratio of 0.1~10:1, heat degradation caused by light with extremely high light density can effectively be prevented if the fluorescent material contains at least one type of material selected from a group including alkali earth metal halogen apatite, alkali earth metal aluminate, oxynitride or nitride, and the rare earth aluminate, and particularly if the fluorescent material contains at least one type of material selected from a group including LAG, BAM, BAM: Mn, YAG, CCA, SCA, SCESN, SESN, CESN, and $CaAlSiN_3$:Eu.

Figure 2:
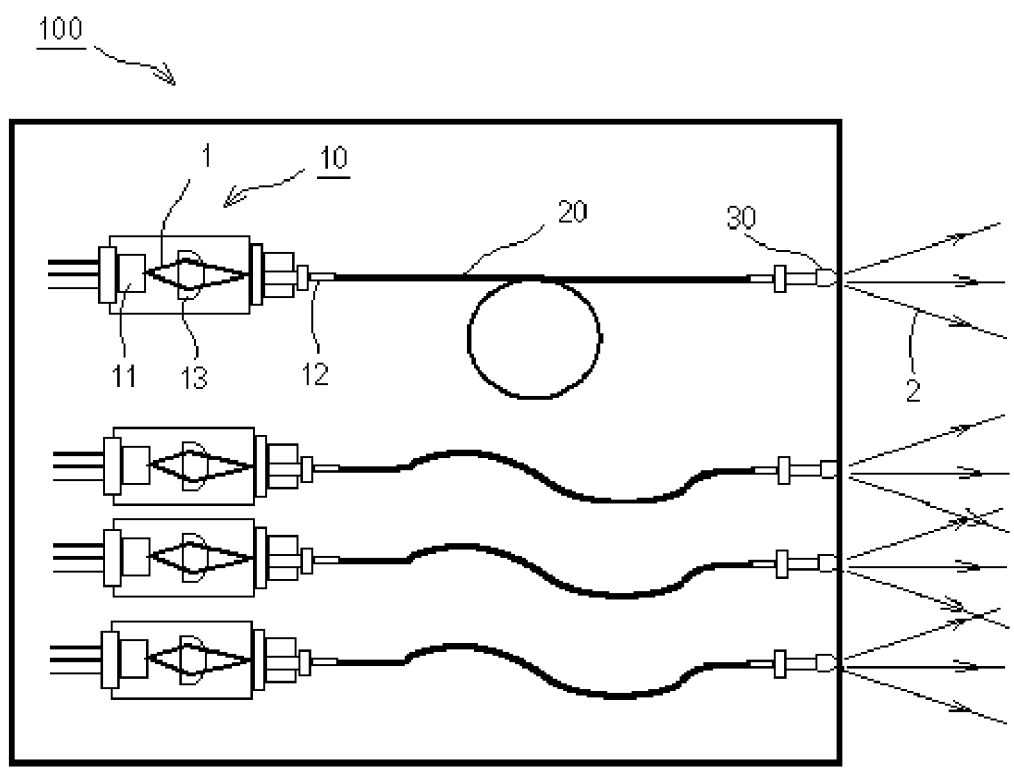
FIG. 2 is a schematic diagram which shows the light emitting device of the present invention.

As shown in FIG. 1, the light emitting device of the present invention primarily comprises, for instance, an excitation light source 10, a light guide 20, and a wavelength converting member 30 as a unit. This unit may alone make up the light emitting device, in which case a mode scrambler (not shown in the figures) is preferably also provided. Alternately, two or more units may be combined such as the four units combined in FIG. 2 to form a light emitting device 100. The number of units combined can be determined by the color rendering properties and the output. The light emitting device of the present invention preferably uses units which each have a brightness of approximately 120 lumens/mm$^2$ or higher.

Excitation Light Source

As shown in FIG. 1, any one of 1st to 3rd excitation light sources comprises light emitting elements 11 or the like, and is constructed such that the light radiated from the light emitting elements 11 is guided from the radiating part 12 to the light guide 20.

The excitation light source is a light source which emits excitation light. Excitation light herein also includes laser diode elements which emits a light that can excite a fluorescent material which will be discussed later.

The first excitation light source (hereinafter also referred to as first laser element) which is a component of the first unit radiates excitation light in the blue wavelength band. This first laser element radiates excitation light in a range of 400-500 nm, 420-500 nm, 430-500 nm, 430-480 nm, 440-470 nm, or 440-460 nm, or in other words, preferably has a linear spectrum within these ranges. Thus, a light emitting device which has extremely high light emitting output can be attained. Furthermore, as will be described later, a light emitting device which has very high light emitting output can be obtained by using fluorescent materials which have good wavelength converting efficiency. Moreover, light of various colors and light with high color rendering properties can be obtained.

The second excitation light source (hereinafter also referred to as the second laser element) which is a component of the second unit used in combination with the first unit is not restricted in particular so long as the excitation light radiated therefrom has a shorter wavelength than that of the first laser element. The second laser element radiates excitation light in a range such as 350~500 nm, 360-460 nm, 360-420 nm, 370-420 nm, 380-420 nm, 380-440 nm, or 380-420 nm, and preferably has a linear spectrum within this range.

The combination of the first laser element and second laser element may combine for instance a 440 nm band and a 400 nm band, and more specifically may combine a 445 nm±15 nm band and a 405 nm±15 nm band, or may combine a 445 nm ±15 nm band and a 375 nm±15 nm band. Furthermore, with the present invention, a third laser element may also be combined, and a preferable combination would be for instance a 445 nm±15 nm band and a 375 nm±15 nm band and a 375 nm±15 nm band.

The laser element itself may be in a laser element which is manufactured by any method and construction commonly known in this field, and normally is constructed by laminating a semiconductor layer over a substrate.

As substrates, a sapphire substrate which has a C surface, R surface and A surface is preferably used in order to form a nitride semiconductor with good crystalline properties with high productivity. Furthermore, as is conventionally known, a nitride semiconductor may be grown on materials other than a nitride semiconductor that are capable of growing a nitride semiconductor, for instance, an insulative substrate such as spinel (MgAl$_2$O$_4$) which forms a main surface of any one of the C surface, R surface or A surface; SiC (including 6H, 4H, and 3C); ZnS; ZnO; GaAs; Si; GaN; and oxide substrates or the like which are lattice matched with a nitride semiconductor. In addition, the substrate may be off-angle, and in this case, the off-angle substrate preferably has one or more directions in a step configuration so that the base layer formed from gallium nitride can be grown with good crystalline properties.

If a different substrate from a nitride semiconductor is used, after growing the nitride semiconductor (buffer layer, base layer, or the like) which forms the base layer prior to forming the element structure on the different substrate from a nitride semiconductor, the different substrate may be removed by a method such as polishing to make a nitride semiconductor (such as GaN) with a single substrate, or the different substrate may be removed after forming an element structure.

By forming a base layer comprising a buffer layer (low temperature growth layer) and/or a nitride semiconductor (preferably GaN) or the like on a different substrate, the growth of the nitride semiconductor which composes the element structure will be favorable, and light in the ultraviolet band can be efficiently emitted by the pn junctions made from these nitride semiconductors.

A non-monocrystalline layer grown at low temperature, such as GaN, AlN, or GaAlN, or the like may be used as a buffer layer.

ELOG (epitaxially laterally overgrowth) growth may be used for the base layer (growth substrate) established on the different substrate. For instance, this can be achieved by optionally growing a nitride semiconductor layer on the different substrate and forming (to be nearly perpendicular to the orientation flat surface of the substrate) thereon a mask field with a stripe configuration or the like using a protective film (such as SiO$_2$ or the like) onto which a nitride semiconductor is not easily grown as well as forming a no-mask field for growing the nitride semiconductor such that the nitride semiconductor layer is grown over this protective layer. By growing the nitride semiconductor from the no-mask field, the nitride semiconductor will also growth in the mask field so that a nearly flat semiconductor layer can be formed by selective growth, or in other words, because growth in the lateral direction will occur in addition to growth in the film thickness direction. Alternatively, the same can be achieved by forming an opening region in the nitride semiconductor layer which has been grown on the different substrate and forming a nitride semiconductor layer on the substrate which includes this opening region. In other words, nitride semiconductor growth will occur in the lateral direction from the side surface of the opening region, and therefore a nearly flat semiconductor layer can be formed.

The semiconductor formed on this substrate may be any type of semiconductor including BN, SiC, ZnSe, GaN, InGaN, InAlGaN, AlGaN, BAlGaN, and BInAlGaN or the like. Similarly, Si, Zn, or the like may be added as an impurity element to the above elements to make a center of light emission.

In particular, nitride semiconductors, and especially Group III nitride semiconductors (such as nitride semiconductors containing Al and Ga, and nitride semiconductors containing In and Ga, $In_XAl_YGa_{1-x-y}N$, $0 \leq X$, $0 \leq Y$, $X+Y \leq 1$) are more suitable as light emitting layer materials which can efficiently emit light in the band from the ultraviolet band to a visible short wavelength band (for instance blue) where fluorescent materials can efficiently become excited. Furthermore, some of the gallium nitride compound type semiconductor may be replaced with B or P. The emission light wavelength from the light emitting element obtained can be adjusted by appropriately setting the types of semiconductor and the mixing ratio thereof. For instance, depending on the composition of the active layer, light which has a main emission peak wavelength between approximately 350 to 550 nm and preferably between approximately 350 to 500 nm or 360 to 500 nm can be obtained, and in particular, light which has a main emission peak wavelength within a range of 420 to 490 nm can be obtained by changing the In content of the active layer.

The semiconductor layer may have a single layer, but homostructures having MIS junctions, PIN junctions, or PN junctions or the like, heterostructures, and double heterostructures are preferably used. Furthermore, a multilayer laminate structure or an ultra lattice structure are also acceptable, as are a single quantum well structure or a multiquantum well structure laminated as a thin film which generates quantum effects.

The semiconductor layer may have a laminate double heterostructure or the like with a first contact layer of n-type gallium nitride, a first clad layer of n-type aluminum gallium nitride, a multiquantum well structure active layer with a plurality of lamination layers consisting of a well layer of indium nitride aluminum gallium or InGaN and a barrier layer of aluminum nitride gallium or GaN, a second clad layer of p-type aluminum nitride gallium, and a second contact layer of p-type gallium nitride, in order.

These semiconductor layers may be formed using a known technology such as Metal Organic Chemical Vapor Deposition (MOCVD), Hydride Vapor Phase Epitaxy (HVPE), or Molecular Beam Epitaxy (MBE) or the like. The film thickness of the semiconductor layer is not restricted in particular, and a variety of film thickness is can be used.

Note that nitride semiconductors have n type conductivity without being doped with impurities. If n-type nitride semiconductors are formed in order to increase the light emitting efficiency or the like, Si, Ge, Se, Te, or C or the like are preferably introduced, as appropriate, as the n-type dopant. On the other hand, when forming a p-type nitride semiconductor, doping with a p-type dopant such as Zn, Mg, Be, Ca, Sr, or Ba or the like is preferable. For instance, impurity concentrations of approximately $10^{15}$ to $10^{21}/cm^3$ and particularly $10^{17}$ to $10^{20}/cm^3$ at the contact layer are exemplified. A nitride semiconductor is difficult to change to a p-type semiconductor simply by doping with a p-type dopant, so after introducing the p-type dopant, preferably the resistance is further dropped by annealing in a furnace or by plasma irradiation or the like.

For instance, an n-type contact layer which is an n-type nitride semiconductor layer, a crack preventing layer, an n-type clad layer, and an n-type light guide layer are formed on the substrate over an optional buffer layer. Excluding the n-type clad layer, the other layers can be omitted depending on the element. The n-type nitride semiconductor layer must have a bandgap which is wider than the active layer at least in the region which contacts the active layer, and therefore a composition which contains aluminum is preferable. For instance, an n-type $Al_yGa_{1-y}N$ ($0 \leq y \leq 1$) layer (value of y may be different for each layer) may be exemplified. Each layer may be grown while doping with an n-type impurity and made to be n-type, or maybe grown without doping and made to be n-type.

An active layer is formed over the n-type nitride semiconductor layer. The active layer preferably has an MQW structure wherein an $In_{x1}Al_{y1}Ga_{1-x1-y1}N$ well layer ($0 \leq x1 \leq 1$, $0 \leq y1 \leq 1$, $0 \leq x1+y1 \leq 1$) and an $In_{x2}Al_{y2}Ga_{1-x2-y2}N$ barrier layer ($0 \leq x2 \leq 1$, $0 \leq y2 \leq 1$, $0 \leq x2+y2 \leq 1$, $x1>x2$) are repeatedly alternatingly layered an appropriate number of times in order of barrier layer/well layer/barrier layer. Normally barrier layers are on both sides of the active layer.

The well layer is formed undoped. On the one hand, except for the final barrier layer adjacent to the p-type nitride semiconductor layer, all of the barrier layers are doped (preferably $1 \times 10^{17}$ to $1 \times 10^{19}/cm^3$), with an n-type impurity such as Si or Sn or the like, and the final barrier wall is grown undoped.

Note that p-type impurities such as Mg or the like from the adjacent p-type nitride semiconductor layer are diffused in the final barrier layer (for instance at a concentration of $1 \times 10^{16}$ to $1 \times 10^{19}/cm^3$). By doping n-type impurities into the barrier layers excluding the final barrier layer, the initial electron concentration in the active layer will be higher and electron injection efficiency to the well layers will also be higher, and the light emitting efficiency of the laser will be increased. On the other hand, the final barrier layer is closest to the p-type nitride semiconductor side and therefore does not contribute to injecting electrons to the well layer. Therefore, by not doping the final barrier layer with n-type impurities but rather essentially doping by diffusing p-type impurities from the p-type nitride semiconductor layer, the efficiency for hole injection into the well layer can be increased. Furthermore, by not doping the final barrier layer with n-type impurities, mixing of differing types of impurities in the barrier layer which reduces the mobility of the carrier can be prevented. When growing the final barrier layer, the growth may be performed while doping with p-type impurities such as Mg or the like at a concentration of $1 \times 10^{19}/cm^3$ or lower. In order to suppress the effect of decomposing the active layer which contains In by gas etching when growing the p-type nitride semiconductor, the final barrier layer is preferably formed to be thicker than the other barrier layers. For instance, a thickness between 1.1 and 10 times the other barrier layers is preferable and a thickness between 1.1 and 5 times the other barrier layers is more preferable.

A p-type electron containment layer, p-type light guide layer, p-type clad layer, and p-type contact layer are formed as a p-type nitride semiconductor layer on the final barrier layer. Except for the p-type clad layer, the other layers may be omitted depending on the element. The p-type nitride semiconductor layer must have a bandgap which is wider than the active layer at least in the region which contacts with the active layer, and therefore formulations which contain Al are preferable. For instance, a p-type $Al_zGa_{1-z}N$ ($0 \leq z \leq 1$) layer (Value of z may differ for each layer) may be exemplified. Thereby a so-called double heterostructure is formed. Furthermore, each layer may be grown while doping with a p-type impurity to make p-type, and diffusing p-type impurities from other adjacent layers to make p-type is also acceptable.

The p-type electron containment layer is made from a p-type nitride semiconductor with an Al mixing ratio higher than that of the p-type clad layer, and preferably is formulated from $Al_xGa_{1-x}N$ ($0.1 \leq x \leq 0.5$). Furthermore, p-type impurities such as Mg or the like have a high concentration and doping is preferably performed at a concentration of $5 \times 10^{17}$ to $1 \times 10^{19}/cm^3$. Therefore, the p-type electron containment layer can effectively contain electrons in the active layer, and the threshold value of the laser can be reduced. Furthermore, the p-type electron containment layer may be grown to a thin-film of approximately 30 to 200 Angstroms, and if thin, the film can be grown at temperatures lower than the p-type light guide layer or the p-type light clad layer. Therefore, by forming the p-type electron containment layer, decomposition of the active layer which contains In can be suppressed as compared to when directly forming the p-type light guide layer or the like on the active layer.

Furthermore, the semiconductor light emitting element may be a semiconductor laser element which has a ridge stripe being formed on the upper side of the active layer (partway to the p-type light guide layer), an active layer being between the guide layers and/or a resonator end face. Furthermore, a protective layer, p-electrode, n-electrode, p pad electrode and n pad electrode or the like may also be formed.

In particular, if the second electrode is formed on the second contact layer, the second electrode is preferably formed on nearly the whole surface as an ohmic electrode. Furthermore, the second electrode is preferably adjusted the sheet resistance as Rp>Rn in which Rp is the sheet resistance of the second electrode and Rn is the sheet resistance of the first contact layer, for instance the n-type contact layers. Normally, the n-type contact layer for instance is formed with a film thickness between 3 and 10 μm, and particularly between 4 and 6 μm, so the sheet resistance Rn is estimated to be between 10 and 15 ohms/square, and therefore a thin film is preferably formed so that Rp has a sheet resistance higher than this. Specifically, a range of 150 μm or more may be exemplified for the second electrode.

In this manner, when the p-type electrode and the n-type electrode have a relationship such that Rp>Rn, a p side pad electrode which has an extension conductor is preferably established on the p electrode in order to diffuse current across the whole p layer in order to efficiently emit the light from the whole active layer. Thereby the external quantum efficiency can be further increased. The shape of the extension conductor is not restricted in particular, and for instance may be linear, curved, lattice, branched, ancyroid, or mesh or the like. These configurations are preferable because the area which blocks the light can be reduced. The p side pad electrode has increased light shielding properties in comparison to the total area so the line width and length is preferably designed so that the light shielding effect is not stronger than the light emission enhancing effect.

Furthermore, the second electrode is preferably formed from a translucent material. For instance, a metallic or alloy single layer film or multilayer film which includes ITO, ZnO, $In_2O_3$, $SnO_2$, gold and one type element selected from platinum family elements may be exemplified. In particular, if the second electrode is formed from a multiple layer film or an alloy film made from a metallic or an alloy including at least one element selected from a group of gold and platinum family elements, and another type of element, the sheet resistance Rp of the p electrode can be adjusted depending on the content of gold or platinum family elements included therein, and therefore the stability and reproducibility of the electrode can be improved. However, gold and platinum elements have high absorption values in the 300 to 550 nm wavelength band, so the transparency can be improved by reducing the content thereof. The relationship between Rp and Rn can be determined by the condition of the light intensity distribution when the light emitting element is emitting light.

If an insulating substrate is used, a laser element made from a nitride semiconductor can be formed by etching from the front surface side of a p-type nitride semiconductor layer, exposing an n-type nitride semiconductor layer, forming a first and second electrode on the p-type and n-type nitride semiconductor layers respectively, and then cutting into chips. Furthermore, if the insulating substrate is removed or if a conductive substrate is used, etching is not necessary for exposing the aforementioned n-type nitride semiconductor layer, and the second electrode may be formed on the front surface of the substrate and the first electrode may be formed on the back surface of the substrate.

In particular, as the third excitation light source which composes the light emitting devices equipped with a mode scrambler which will be discussed later, any light may be used so long as the light can excite a fluorescent material to be discussed later. The excitation light source may use a device which is an energy source for the aforementioned semiconductor light emitting elements, lamps or the like, as well as electron beams, plasma, and EL or the like. Of these, the use of semiconductor light emitting elements is preferable. Semiconductor light emitting elements make possible compact light emitting devices with good power efficiency because the light emitting intensity is high. Furthermore, a light emitting device can be obtained which has excellent initial drive properties and is robust against vibration or repeated on-off switching. Semiconductor light emitting elements may be light emitting diode elements (LED) or laser diode elements (LD) or the like, but of these, laser diode elements are preferable. These laser diode elements make possible light emitting devices which have extremely high light emitting output. For instance, a device which radiates light with a main light emitting peak wavelength of approximately 350 nm to 550 nm is preferable. Thereby, as will be discussed later, fluorescent materials with good wavelength converting efficiency can be used, and as a result, a light emitting device with high light emitting output can be obtained while obtaining light with a variety of colors. Furthermore, degradation of the wavelength converting member, which will be discussed later, can be prevented, and a light emitting device with long life and high reliability can be obtained.

Light Guide

Any one of 1st to 3rd light guides transfers the light radiated from the excitation light source, and preferably guides the light to the wavelength converting member. Therefore one end and/or the other end of the light guide is positioned at the excitation light source or the wavelength converting member, and preferably one end is positioned at the excitation light source and the other end at the wavelength converting member.

The light guide can be freely changed to any length, and the shape can be changed freely, and in particular, bending around curves and corners is possible, so the light can be guided to any desired location. Therefore, so long as this property is possible, any material and construction may be used. In particular, guiding the light radiated from the excitation light source to the wavelength converting member without damping is preferable from the viewpoint of energy efficiency.

The light guide may for instance be an extremely fine glass fiber which is used as a transfer path for light when transferring the light, and a combination of materials which have a high refraction index and materials which have a low refraction index, or materials which have high reflectivity may be used. Of these materials, double layer materials with a cross-section where the center region (core) is surrounded by a surrounding region (clad) are preferable, and a material where the refraction index of the core is higher than the refraction index of the clad is more preferable from the viewpoint that a light signal can be transferred without damping. The light guide preferably has a core which occupies a larger area than the clad, from the viewpoint of reducing light density at the end of the light guide. Furthermore, the light guide preferably has a small diameter clad from the viewpoint of preventing light from returning to the light guide. For instance, a core diameter of approximately 1000 μm or less and a clad diameter (including the core diameter) of approximately 1200 μm or less may be exemplified, but a core diameter of approximately 400 μm or less and a clad diameter (including the core diameter) of approximately 450 μm or less is preferable. Specifically, a ratio of core/clad=114/125 (μm) or 72/80 (μm) or the like may be exemplified.

The light guide may be either a monofiber or a multifiber, but a monofiber is preferable. Furthermore, either a single mode fiber or a multimode fiber may be used, but a multimode fiber is preferable.

The material of the light guide is not restricted in particular, and for instance may be quartz glass or plastic or the like. Of these, the core material is preferably constructed from pure silica (pure quartz). Thereby transmission losses can be suppressed.

Figure 3:
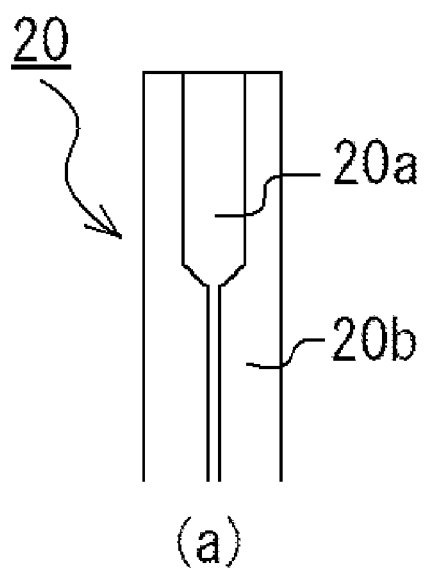
FIGS. 3(a) and 3(b) are schematic diagrams for describing the structure of the end region of the fiber for the light emitting device of the present invention.
Figure 3:
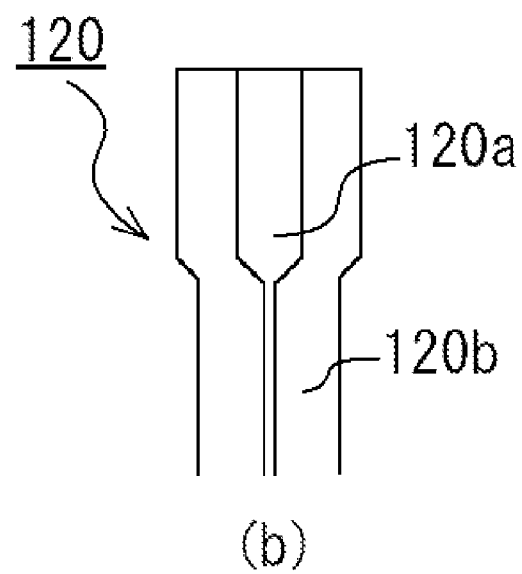

Furthermore, from the viewpoint of reducing light density at the light guide ends, as shown in FIG. 3(a) and (b), the light guide may have a core diameter at the ends of the light guide 20, 120 which is wider than the core 20a, 120a in the middle region, and for instance, a TEC fiber (clad 20b diameter is fixed), or a taper fiber (clad 120b diameter is tapered) or the like where the core diameter at the ends is approximately 1.05 to 2.0 times the core diameter in the middle region may be exemplified. Thereby degradation of the fiber at the ends of the light guide can be prevented. Furthermore, degradation of the wavelength converting member or the like located at the end of the light guide can be prevented and light can be consistently and efficiently radiated onto the wavelength converting member.

Furthermore, photonic crystal fiber which has one or more air voids or air holes in the core or the clad (Refer to Osamu Toyama, "Photonics Crystal Fiber" Proceedings of 31st Meeting on Lightwave Sensing Technology, LST 31-14, page 89-96, Jun. 6, 2003; Photonics Crystal Fiber DIAGUIDEOR-PCF, Mitsubishi Cable Industries, Ltd., Product Catalog, No. 6-184 (2003.01)), also known as index guiding, photonics bandgap, or hole assisted or the like, may also be used. In order to prevent moisture or the like from permeating into the air holes in photonics crystal fiber, the ends are covered with a predetermined material. Therefore light which has been transferred by the light guide will easily be radiated beyond the width of the core at the end. In any case, the light density at the end of the light guide can be reduced, and therefore the effects of the present invention can more easily be obtained.

Note that the light guide is not necessarily restricted to one unit, and several light guides may be connected in series or parallel. In particular, for light emitting devices equipped with a mode scrambler which will be discussed later, a light guide with a mode scrambler and a light guide without a mode scrambler may be connected.

Wavelength Converting Member

Any one of the 1st to 3rd wavelength converting members absorbs part or all of the excitation light radiated from the excitation light source, converts the wavelength, and can emit light with a wavelength band longer than the excitation light from the laser elements and has a light emission spectrum containing for instance red, green, blue, as well as intermediary colors thereof such as yellow, blue green, and orange or the like. Therefore, the type of wavelength converting member is not restricted in particular so long as the wavelength converting member is constructed of materials which can achieve this function. In other words, the wavelength converting member converts part or all of the light generated from the excitation light source to light which has a longer light emission peak wavelength, which is then emitted.

The wavelength converting member is preferably constructed from material such that the light obtained from the wavelength converting member can be white light regardless of the wavelength of the excitation light. Furthermore, in order to provide good light rendering properties, the wavelength converting member is preferably constructed from a material where the average color rendering evaluation value (Ra) of the radiated light is 70 or higher, and more preferably 80 or higher.

Color rendering properties herein refers to the property of a certain light source to control the appearance of the colors of an object which is illuminated by that light source, and good light rendering properties generally refers to achieving close to the appearance of the colors of the object when illuminated by sunlight (Refer to Ohmsha Ltd., "Phosphor Handbook", p 429). Color rendering properties can be improved by using a fluorescent material layer to be discussed later in combination with a light emitting element. Furthermore, the average color rendering evaluation value (Ra) is basically determined by the value of the average color shift when 8 types of color indicators are illuminated by a test light source and a standard light source.

The color tone of the light obtained can be adjusted for instance by combining the light of the three primary colors (blue, green, red). Furthermore, the tone can also be adjusted by combining two colors of light which have a complementary color relationship such as blue and yellow, blue green and red, green and red, or blue-purple and yellow-green. Herein, complementary colors refers to two colors which are on opposite sides of the white point of a color chart. Note that the light of each of the colors used for adjusting the color tone is not all necessarily light which has the wavelength converted by the wavelength converting member, and excitation light obtained from the excitation light source may also be used. Furthermore, with the present invention, the relationship between the color of light and the wavelength is in conformance with JIS Z8110.

The wavelength converting member is for instance constructed from a fluorescent material or pigment or the like. In particular, a light emitting device which has excellent light emitting brightness and color rendering properties can be obtained by using fluorescent materials.

Note that, as will be discussed later, the light emitting device of the present invention may have a plurality of wavelength converting members which are integrated together in each unit.

(Fluorescent Material or the Like)

The fluorescent material is not restricted in particular so long as the material is excited by an excitation light from the excitation light source, but preferably at least one type and more preferably a combination of two types of fluorescent materials are used for each excitation light. Examples of various fluorescent materials include:

(i) alkali earth metal halogen apatite
(ii) alkali earth metal borate halogen
(iii) alkali earth metal aluminate
(iv) oxynitrides or nitrides
(v) alkali earth silicates and alkali earth nitride silicates
(vi) sulfides
(vii) alkali earth thiogallate
(viii) germinate
(ix) rare earth aluminate
(x) rare earth silicate
(xi) organic compounds and organic complexes or the like which are primarily activated by lanthanoids such as Eu.

(i) Alkali earth metal halogen apatite fluorescent materials are preferably those which are primarily activated by lanthanoids such as Eu or transition metal elements such as Mn, such as $M_5(PO_4)_3X:RE$ (where M is one or more elements selected from Sr, Ca, Ba, Mg, and Zn; X is one or more elements selected from F, Cl, Br, and I; and RE is Eu and/or Mn).

For instance, calcium chlorapatite (CCA) and barium chlorapatite (BCA) or the like may be exemplified, and specifically, $Ca_{10}(PO_4)_6Cl_2:Eu$, and $(Ba, Ca)_{10}(PO_4)_6Cl_2:Eu$ or the like may be exemplified.

(ii) Examples of alkali earth metal borate halogen fluorescent materials are $M_2B_5O_9X:RE$ (where M, X, and RE are defined as shown above) or the like.

For instance, calcium chlorborate (CCB) or the like may be exemplified, and specifically $Ca_2B_5O_9Cl$:Eu or the like may be exemplified.

(iii) Examples of alkali earth metal aluminate fluorescent materials are europium activated strontium aluminate (SAE) and europium activated barium magnesium aluminate (BAM), as well as $SrAl_2O_4$:$R_E$, $Sr_4Al_4O_{25}$:$R_E$, $CaAl_2O_4$:$R_E$, $BaMg_2Al_{16}O_{27}$:$R_E$, and $BaMgAl_{10}O_{17}$:$R_E$ (where RE is defined as shown above) or the like.

(iv) Oxynitride fluorescent materials are preferably those primarily activated by rare earth elements, and contain at least one Group II element and at least one Group IV element. Combinations of these elements are not restricted in particular, and examples include those expressed by the following formulations:

$L_xJ_yO_zN_{((2/3)x+(4/3)y-(2/3)z)}$:R or
$L_xJ_yQ_tO_zN_{((2/3)x+(4/3)y+t-(2/3)z)}$:R (where L is at least one type of Group II elements selected from a group consisting of Be, Mg, Ca, Sr, Ba, and Zn; J is at least one type of Group IV elements selected from a group consisting of C, Si, Ge, Sn, Ti, Zr, and Hf; Q is at least one type of Group III elements selected from a group consisting of B, Al, Ga, and In; R is at least one type of rare earth elements selected from a group consisting of Y, La, Ce, Pr, Nd, Sm, Eu, Gd, Tb, Dy, Ho, Er, Lu, Sc, Yb, and Tm; and $0.5 \leq x \leq 1.5$, $1.5 \leq y \leq 2.5$, $0 \leq t \leq 0.5$, and $1.5 \leq z \leq 2.5$.)

If x, y, and z in the equation are within the aforementioned ranges, high brightness will be obtained, and in particular, oxynitride fluorescent materials where $x=1$, $y=2$, and $z=2$ have higher brightness, and are more preferable. However, the above range is not a restriction and other materials may be used.

Specifically, oxynitride fluorescent materials which use alpha sialon as the base material, oxynitride fluorescent materials which use beta sialon as the base material, and Eu activated calcium aluminum silicon nitride expressed by the formula $CaAlSiN_3$:Eu or the like may be exemplified.

Nitride fluorescent materials are preferably those activated by the rear rare elements. These fluorescent materials may be nitride fluorescent materials which include at least one type of the aforementioned Group II elements, at least one type of the aforementioned Group IV elements, and N, where B is within a range of 1 to 10,000 μm. Alternatively, oxygen may also be included in the nitride fluorescent material formulation.

Of the aforementioned materials, nitride fluorescent materials containing Ca and/or Sr, Si, and N, such as calcium silicon nitride (CESN), strontium silicon nitride (SESN), and calcium strontium silicon nitride (SCESN), and particularly those activated by Eu and those where B is within a range of 1 to 10,000 μm are preferable. A portion of the Eu may be replaced by at least one type of the aforementioned rare earth elements. A portion of the Ca and/or Sr may be replaced by at least one or more of the aforementioned Group II elements. A portion of the Si may be replaced by at least one type of the aforementioned Group IV elements.

Specifically, these nitride fluorescent materials are expressed by the equations $L_xJ_yN_{((2/3)x+(4/3)y)}$:R or
$L_xJ_yO_zN_{((2/3)x+(4/3)y-(2/3)z)}$:R (where L, J, and R are as defined above; and x, y, and z are such that $0.5 \leq x \leq 3$, $1.5 \leq y \leq 8$, and $0 \leq z \leq 3$), and B is preferably within a range of 1 to 10,000 μm.

Examples of alkali earth silicates and alkali earth nitride silicates include $M_2Si_5N_8$:Eu,
$MSi_7N_{10}$:Eu,
$M_{1.8}Si_5O_{0.2}N_8$:Eu, and
$M_{0.9}Si_7O_{0.1}N_{10}$:Eu (where M is as defined above).

(vi) Examples of sulfites include alkali earth sulfides such as CaS:Eu and SrS:Eu or the like as well as $La_2O_2S$:Eu, $Y_2O_2S$:Eu, $Gd_2O_2S$:Eu, ZnS:Eu, ZnS:Mn, ZnCdS Cu, ZnCdS:Ag/Al, ZnCdS:Cu/Al or the like.

(vii) Examples of alkali earth thiogallate include $MGa_2S_4$:Eu (where M is as defined above).

(viii) Examples of germinate include 3.5 MgO-0.5 $MgF_2$-$GeO_2$:Mn, and $Zn_2GeO_4$:Mn or the like.

(ix) Rare earth aluminates are preferably those primarily activated by lanthanoid elements such as Ce, for example yttrium aluminum garnet (YAG) and lutetium aluminum garnet (LAG), and specifically includes $Y_3Al_5O_{12}$:Ce, $(Y_{0.8}Gd_{0.2})_3Al_5O_{12}$:Ce, $Y_3(Al_{0.8}Ga_{0.2})_5O_{12}$:Ce, $(Y,Gd)_3(Al,Ga)_5O_{12}$:Ce, $Y_3(Al,Sc)_5O_{12}$:Ce, and $Lu_3Al_5O_{12}$:Ce (as well as those where all or part of Y is replaced by Lu and those where all or part of the Ce is replaced by Tb) as well as $Tb_3Al_5O_{12}$:Ce, and $Gd_3(Al,Ga)_5O_{12}$:Ce.

(x) Rare earth silicates include $Y_2SiO_5$:Ce, and $Y_2SiO_5$:Tb or the like.

(xi) Organic compounds and organic complexes are not restricted in particular, and any commonly known material may be used. Materials which are primarily activated by a lanthanoid element such as Eu or the like are preferable, but at least one type selected from a group consisting of the aforementioned rare earth elements as well as Cu, Ag, Au, Cr, Co, Ni, Ti, and Mn may be used in place of or in addition to Eu.

Of these materials, particularly preferable are: (ix) rare earth aluminate fluorescent materials primarily activated by lanthanoid elements such as Ce, specifically YAG type fluorescent materials expressed by the formulations $Y_3Al_5O_{12}$:Ce, and $(Y,Gd)_3Al_5O_{12}$:Ce or the like (including compounds where all or part of Y is replaced by Lu, and compounds where all or part of the Ce is replaced by Tb); and (iv) oxynitride and nitride fluorescent materials primarily activated by rare earth elements, specifically having a general formula of $L_xJ_yN_{((2/3)x+(4/3)y)}$:R or
$L_xJ_yO_zN_{((2/3)x+(4/3)y-(2/3)z)}$:R (where L, J, R, x, y, and z are as defined above).

The rare earth aluminate fluorescent materials have high heat durability and therefore can discharge stable light, and also have good wavelength converting efficiency, and can therefore efficiently emit light. Furthermore, nitride fluorescent materials are excited by ultraviolet light and light on the short wavelength side of visible light, and can emit light to the long wavelength side of visible light, and therefore have good color rendering properties. Furthermore, by using a combination of these fluorescent materials, light which has good color rendering properties and which has an average color rendering evaluation value (Ra) of for instance 80 or higher can be obtained.

Furthermore, particularly preferable are:
combinations of (ix) YAG together with at least one type of (i) CCA, (ii) CCB, and (iii) BAM;
combinations of (iii) SAE and (i) CCA: Mn;
combinations of (iii) SAE and (iv) SESN;
combinations of (iii) SAE and (iv) SCESN;
combinations of (iii) SAE and (iv) CESN;
combinations of (i) CCA, (ix) LAG, and (iv) SESN;
combinations of (i) CCA, (ix) LAG, and (iv) SCESN;
combinations of (i) CCA, (ix) LAG, and (iv) CESN;
combinations of (i) CCA, (ix) LAG, and (iv) $CaAlSiN_3$:Eu;
combinations of (ix) LAG, and (iv) SESN;
combinations of (ix) LAG, and (iv) SCESN;
combinations of (ix) LAG, and (iv) CESN; and combinations of (ix) LAG, and (iv) CaAlSiN$_3$:Eu.

Thus, both good light emitting efficiency and excellent color rendering properties can be achieved.

In particular, the first laser element is preferably a combination of the last two combinations. The second laser element is preferably a combination of the first five combinations, and in particular, combinations with (i) CCA and (ix) LAG and (iv) SESN or combinations with (i) CCA and (ix) LAG and (iv) SCESN are more preferable. Thereby both high efficiency and excellent color rendering properties can be achieved.

Furthermore, from another viewpoint, the fluorescent material preferably contains at least some material with good temperature characteristics. Herein, material with good temperature characteristics refers to materials which do not experience a noticeable drop in brightness even when the temperature of the wavelength converting member increases because of laser light illumination, when compared to the brightness of the wavelength converting member at room temperature. Specifically, wavelength converting members have a brightness retention rate at 250° C. which is 50% or greater than the brightness retention ratio at room temperature (25° C.), preferably 55% or greater, 60% or greater, 65% or greater, or 70% or greater. Furthermore, the wavelength converting members have a brightness retention rate at 300° C. which is 30% or greater than the brightness retention ratio at room temperature, preferably 35% or greater, 40% or greater, 45% or greater, or 50% or greater. More preferable are wavelength converting members which have a brightness retention rate at 250° C. which is 50% or greater than the brightness retention ratio at room temperature, preferably 55% or greater, 60% or greater, 65% or greater, or 70% or greater as well as have a brightness retention rate at 300° C. which is 30% or greater than the brightness retention ratio at room temperature, preferably 35% or greater, 40% or greater, 45% or greater, or 50% or greater.

These fluorescent materials preferably have at least one type of material selected from a group consisting of alkali earth metal halogen apatite, alkali earth metal aluminate, oxynitrides or nitrides, and rare earth aluminates, and representative examples include LAG, BAM, YAG, CCA, SCA, SCESN, SESN, CESN, and CaAlSiN$_3$:Eu or the like. Of these materials, LAG, BAM (particularly those activated by Mn), and CaAlSiN$_3$:Eu or the like are preferable. Thereby higher brightness can be achieved.

Note that besides the aforementioned fluorescent materials, other fluorescent materials which have the same performance and effect may also be used.

As will be discussed later, if two or more types of fluorescent materials are used in combination, each fluorescent material may be used independently, such as added to a coating material, or two or more may be combined and added to the coating material. In this case, the ratio of the fluorescent material used in each combination can be appropriately adjusted depending on the wavelength of the excitation light source used, the light emitting intensity, and the tone or the like of the light to be obtained.

For instance, if a combination of LAG and SESN, SCESN or CaAlSiN$_3$:Eu is used, the materials will be combined at a weight ratio within a range of approximately 50:1 to 1:50, and more preferably combined at a weight ratio within a range of approximately 30:1 to 1:30, 50:1 to 1:1, or 30:1 to 1:1 respectively. Furthermore if a combination of LAG and CCA and SESN, SCESN or CaAlSiN$_3$:Eu is used, the LAG and CCA will preferably be combined at a weight ratio of approximately 1:10 to 10:1, and more preferably at a weight ratio of approximately 1:5 to 5:1, 10:1 to 1:1, and 5:1 to 1:1. The LAG, and SESN, SCESN, or CaAlSiN$_3$:Eu may be used in combination within the aforementioned ranges.

A specific form of the wavelength converting member of the present invention preferably uses a combination of LAG (green emitted light) and SCESN or SESN (red emitted light). Therefore, when combined with blue excitation light (light emitting elements which have a light emitting peak within a range of 430 to 500 nm for instance), the three primary colors can be ensured and white emission light can be attained which has good color rendering properties.

A combination of (Sr, Ca)$_5$(PO$_4$)$_3$Cl:Eu (blue emitted light) and LAG or BaSi$_2$O$_2$N$_2$:Eu (green to yellow emitted light) and SCESN (red emitted light); or a combination of CCA, CCB, or BAM (blue emitted light) and YAG (yellow emitted light); or a combination of CCA, CCB, or BAM or the like (blue emitted light) and LAG (green emitted light) and SCESN (red emitted light) are preferably used, arranged in this order from the light incidence side. Therefore, when combined with a light emitting element which has a light emission peak wavelength within the short wavelength range of visible light from 360 to 420 nm, white emission light with good color rendering properties can be provided.

Note that the desired white light can be achieved from the various color light by changing the formulation ratios of the fluorescent materials used. In particular, if a combination of CCA or the like (blue emitted light) and YAG (yellow emitted light) is used, the weight ratio is preferably approximately 1 to 20:1, more preferably approximately 5 to 10:1, and thereby the light emitting efficiency can be increased.

Furthermore, a combination of LAG (green emitted light) and SESN, SCESN, or CaAlSiN$_3$:Eu (red emitted light) is preferably used. Thereby the light emitting efficiency can be further increased by combining with a light emitting element which has a light emission peak wavelength in the neighborhood of 450 nm (such as 420 to 460 nm).

Furthermore, if a fluorescent material which emits yellow light and a fluorescent material which emits red light are used in combination, and if combined with a light emitting element which has an emission peak wavelength in the neighborhood of 450 nm in the short wavelength band of visible light, the mixed color light which is obtained by combining the excitation light discharged from the light emitting elements and the light release from the fluorescent material will be guided externally as light from the wavelength converting member. This light will white light with a reddish hue.

Furthermore, if a fluorescent material which emits green to yellow light is used, a light emitting element which has an emission peak wavelength in the neighborhood of 450 nm (440 to 470 nm), for instance 445 nm, a short wavelength band of visible light will preferably be used in combination. Therefore the light can be made to be white light by combining the excitation light from the light emitting element with yellow light converted from the excitation light. Therefore, absorption of the light during wavelength conversion can be avoided and the light emitting efficiency can be increased.

For the case where a combination of fluorescent material which emits blue light and fluorescent material which emits yellow light is used, by combining with a light emitting element which has an emission peak wavelength near 375 nm in the ultraviolet light band, the light released will be the white light being released from the wavelength converting member. Ultraviolet light is invisible to human eyes so the only light will be the light released from the fluorescent material with a wavelength converted to visible light.

Furthermore, if (1) a light emitting element which has an emission peak wavelength around 400 nm (for instance 370 to 420 nm) in the short wavelength band of visible light is used in combination with (2) a fluorescent material which emits light closer to blue than the light emitting elements (for instance 440 to 460 nm), (3) a fluorescent material which emits green light (for instance 520 to 540 nm) when excited by blue light, (4) a fluorescent material which emits yellow light (for instance 550 to 580 nm) when excited by blue light, and (5) a fluorescent material which emits red light (for instance 640 to 660 nm) when excited by blue light, then the light release from the wavelength converting member will primarily be white light. In particular, these fluorescent materials are preferably arranged in this order from the side of light incidence. With this combination, the light emitting efficiency can be increased. Furthermore, if a combination of (1), (2), and (4) is used, an even higher light emitting efficiency can be achieved. Furthermore, if a combination of (1) through (3) and (5) is used, the color rendering properties can be improved. Note that in these cases, excitation light from the light emitting element was not utilized as a color component of the light, and the white color was obtainable using only light which had been converted by the fluorescent material, so the color temperature and color coordinates were not changed by the light output from the light emitting element, and the white color intensity could be adjusted.

According to the present invention, the first unit and the second unit or the like do not need to be combined as white light units, respectively. In other words, a light emitting device which provides white light with high brightness and good color rendering properties by combining a first unit and a second unit or the like is also acceptable. For instance, the following combinations can be exemplified:

a white light emitting device comprising a green light first unit, which combines (a) a 430 to 500 nm light emitting element and (b) a fluorescent material which emits green light, and a pink light second unit, which combines (c) a 360 to 420 nm light emitting element, (d) a fluorescent material which emits blue light, and (e) a fluorescent material which emits red light;

a white light emitting device comprising a white light first unit which combines (a), (b), and (e), and a blue light second unit which combines (c) and (d); and a white light emitting device comprising a green light first unit which combines (a) and (b), and a red light second unit which combines (c) and (e), and a blue light third unit which combines (c) and (d).

As pigments, dyes and fluorescent dyes such as perylene or the like may be exemplified.

In order to prevent the formation of aggregates and to show maximum light absorbency and light converting efficiency, these fluorescent materials and pigments or the like normally have a particle size in the range of approximately 1 μm to 20 μm, and a range of approximately 2 μm to 8 μm is preferable, and a range of approximately 5 μm to 8 μm is more preferable. Furthermore, by using this type of fluorescent material which has a relatively large particle size, the productivity of the light emitting device can be improved. Herein, the particle size indicates the average particle diameter obtained using the air permeation method. Specifically, in an environment with a temperature of 25° C. and a humidity of 70%, a 1 $cm^3$ test sample is weighed, and after packing into a special tube shaped container, dry air at a fixed pressure is made to flow, and the relative surface area is determined from the pressure differential, and then the average particle size is calculated.

(Coating Material)

Any one of 1st to 3rd wavelength converting member of the present invention can be formed by mixing fluorescent material or the like with a coating material. The coating material may for instance be an inorganic substance such as inorganic glass, yttria sol, alumina sol, or silica sol; or an organic substance such as one or more types of polyolefin resin, polycarbonate resin, polystyrene resin, epoxy resin, acrylic resin, acrylate resin, methacrylic resin (PMMA or the like), urethane resin, polyamide resin, polynorbornene resin, fluoridated resin, silicone resin, modified silicone resin, modified epoxy resin, as well as liquid crystal polymer or the like. These coating materials preferably have excellent heat durability, light durability, weather durability, and transparency. Of these materials, fluoridated resin and silicone resin (particularly dimethylsiloxane and methyl polysiloxane resins) or the like are preferable.

If the wavelength converting member comprises a fluorescent material or the like and a resin which is a coating material, the weight ratio of the fluorescent material or the like and the resin are mixed to be preferably within a range of approximately 0.1 to 10:1, and more preferably within a range of approximately 0.5 to 10:1, 1 to 3:1, or 1.5 to 2.5:1. However, as will be described later, if the wavelength converting member is formed with a laminate structure, the ratio of fluorescent material or the like and resin in each layer does not necessarily have to be the same. For instance, the material used and the ratios thereof may be appropriately adjusted in consideration of the heat durability, weather durability, and refractive index or the like of the fluorescent material as well as the properties of the actual resin or the like.

(Filler)

Any one of 1st to 3rd wavelength converting members of the present invention may be constructed only of fluorescent material or the like as described above, but optionally a filler may be mixed into the coating material. Thereby the wavelength converting member can easily be adhered to the light guide. Furthermore, the wavelength converting member can be uniformly dispersed so that a light emitting device which has minimal color variation can be obtained.

Filler is preferably a material which can reflect, disperse, and/or scatter or the like light which is illuminated from the outside. Thereby the excitation light can uniformly be illuminated onto the fluorescent material or the like, which will have the effect of reducing color variation.

Examples of the filler include silica (fumed silica, sedimentary silica, fused silica, crystalline silica, ultrafine powdered amorphous silica, or silicic anhydride or the like), quartz, titanium dioxide, tin oxide, zinc oxide, tin monoxide, calcium oxide, magnesium oxide, beryllium oxide, aluminum oxide, boric nitride, silica nitride, alumina nitride and other metallic nitrides, SiC and other metallic carbides, calcium carbonate, potassium carbonate, sodium carbonate, magnesium carbonate, barium carbonate and other metallic carbonate, aluminum hydroxide, magnesium hydroxide and other metallic hydroxides, aluminum borate, barium titanate, calcium phosphate, calcium silicate, clay, gypsum, barium sulfate, mica, diatomic earth, white clay, inorganic balloon, talc, lithopone, zeolite, halloysite, fluorescent material, and metal shavings (silver powder) or the like. Furthermore, in order to achieve strength, needle shaped fillers such as potassium titanate, barium silicate, and glass fiber or the like may also be used. Of these, barium titanate, titanium oxide, aluminum oxide, and silicon oxide or the like are preferable.

The particle size of the filler is not restricted in particular, and for instance, filler where the median particle size is greater than 1 μm and less than 5 μm can readily diffusely reflected light from the fluorescent material, and can suppress color variation which easily occurs when using a large diameter fluorescent material or the like. Filler which has a median particle size greater than 1 nm and less than 1 μm will have a slightly lower effect on the light wavelength from the light emitting element, but can increase the viscosity of the coating material such as resin without reducing the luminosity. Therefore fluorescent material or the like can be nearly uniformly dispersed in the resin and be maintained in that condition, and therefore even when using relatively larger diameter fluorescent materials or the like which are difficult to handle, the material can be produced with good yields. When filler with a median particle size greater than 5 μm and less than 100 μm is included in the coating material such as resin, color variation of the light emitting element can be improved because of the effect of light scattering, and the thermal impact durability of the resin can be increased. Note that the filler may have a variety of shapes such as spheres, needles, or flakes, in consideration of the scattering properties and reflection properties or the like.

The filler preferably has approximately the same particle size and/or shape as the fluorescent material or the like. Herein, approximately the same particle size means that the difference between the median particle size of each of the particles is less than 20%, and approximately the same shape means that the difference in the roundness value (roundness=circumferential length of a true circle equal to the projected surface area of the particle/circumferential length of the projection of the particle) which shows the degree of true roundness of each particle is less than 20%. By using this type of filler, the fluorescent material or the like and the filler will mutually interact so that the fluorescent material or the like will be thoroughly dispersed throughout the coating material such as resin, and color variation can be more positively suppressed.

The filler may for instance account for between 0.1 and 80 wt %, and particularly 70 wt % or less, 50 wt % or less, 40 wt % or less, or 30 wt % or less of the total wavelength converting member.

The wavelength converting member is made by mixing the aforementioned fluorescent material or the like together with optional filler in a resin which is the coating material, using an appropriate solvent if necessary, and can be formed to the desired shape by a method such as the potting method, spray method, screen printing method, stencil printing method or the like, as well as plastic molding methods such as the injection method, compression method, transfer method, projection method, extrusion method, lamination method, calendar method, and injection mold method or the like, vacuum coating method, powder spray coating method, electrostatic deposition method, and electric migration deposition method or the like.

Furthermore, the fluorescent material or the like and the optional filler and an appropriate solvent can be mixed together, and using a forming method which pressurizes while optionally heating or electrodeposition or the like without using a coating material.

The wavelength converting member may be formed as a single layer of one type of fluorescent material or the like, or may be formed as one layer of a uniform mixture of two or more types of fluorescent materials or the like, or may be laminated with two or more layers where each layer contains one type of fluorescent material or the like, or may be laminated with two or more layers where each layer contains a uniform mixture of two or more types of fluorescent materials or the like. For the case where two or more single layers are laminated, the fluorescent material or the like contained in each layer may convert the wavelength of the same wavelength of incident light to the same wavelength of radiated light, or may convert incident light with the same wavelength to radiated light with different wavelengths, but the wavelength converting members preferably convert the wavelength of incident light with different wavelengths to radiation light with the same or different wavelengths. Thereby all of the light which is incident on the wavelength converting member and is to be converted can have the wavelength converted, and more efficient wavelength conversion can be performed.

Figure 4:
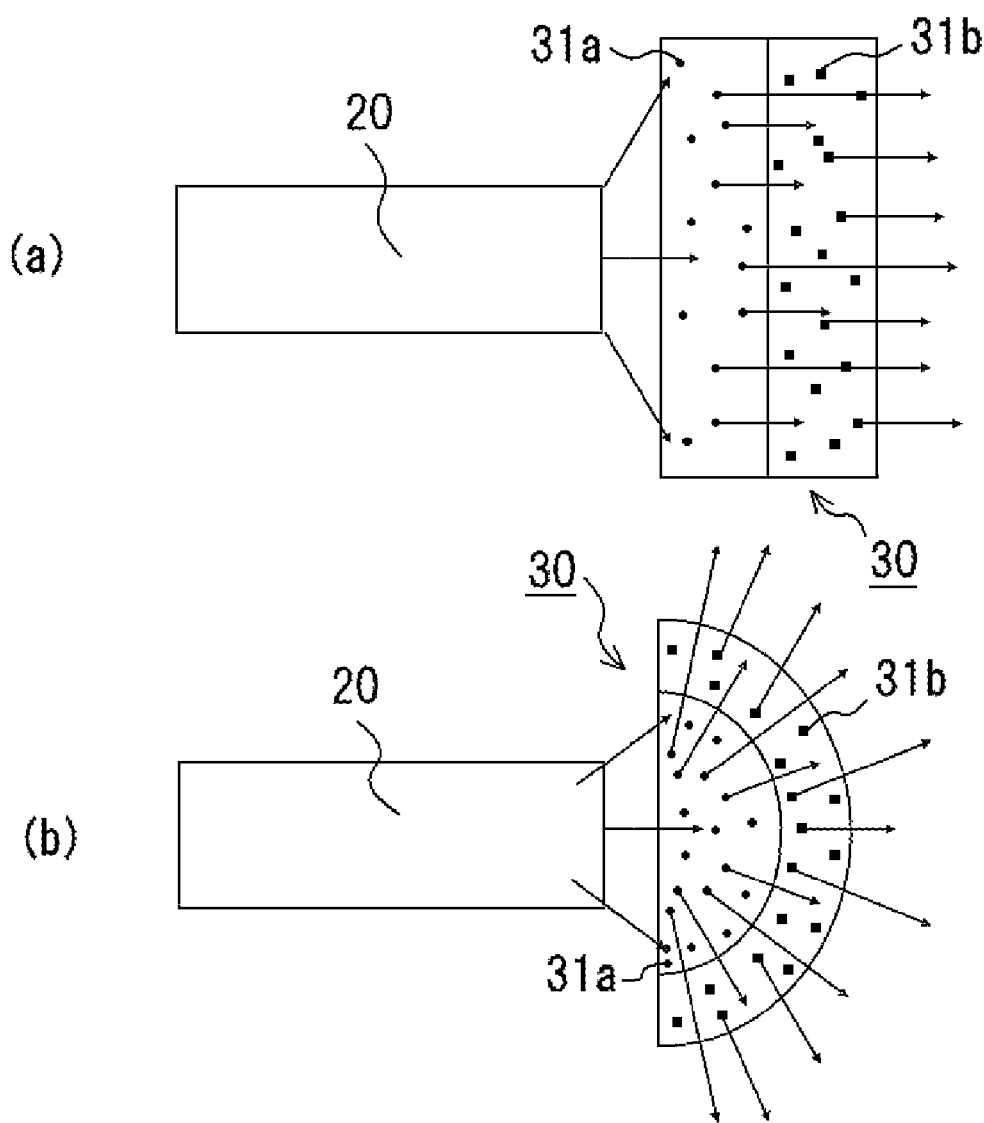
FIGS. 4(a) and 4(b) are schematic diagrams for describing the structure of the wavelength converting member of the light emitting device of the present invention.

As shown in FIG. 4(a), the wavelength converting member 30 may be formed by overlaying sheets containing mutually different types of fluorescent materials 31a, 31b, and as shown in FIG. 4(b), an upper layer containing fluorescent material 31b is overlaid to completely cover a bottom layer which contains a fluorescent material 31a which is different than the fluorescent material 31b. Note that the wavelength converting member 30 preferably has a protruding bowl shape on the radiating side. With this shape, the brightness can be further increased. The film thickness of the wavelength converting member is not restricted in particular, but can be appropriately adjusted based on the materials used. For instance, if the fluorescent material and resin or the like form a thick film, the conversion efficiency will be increased and as a result the light emitting efficiency can also be increased, but on the other hand, the light emitting efficiency will also be hurt by absorption or the like of the light, so an appropriate film thickness is preferably selected with this in mind.

As shown in FIG. 1, the wavelength converting member 30 may be attached to the end of the light guide 20, or in other words the output region 21 in order to guide the excitation light 1, or may be attached to the connection part between the excitation light source 10 and the light guide 20 which is the radiating part 12 for the excitation light 1. The case of the latter may be used even in locations where the tip end of the light guide will get dirty. Furthermore, replacement of the wavelength converting member will be simplified. Furthermore, productivity can be increased by establishing wavelength converting members in various locations.

Furthermore, as will be described later, if a plurality of excitation light sources are used in combination with the first excitation light source and the second excitation light source or the like, the excitation light from each of the excitation light sources will be guided by the light guide and bundled together at the light guide radiating side so that all of the light will be applied to the wavelength converting member by integrating single layers or multiple layers, or partially integrating single layers or multiple layers. Thereby the process of using each of the wavelength converting members can be simplified.

Furthermore, fluorescent material or the like may be included in the core material for instance in a part of the inside of the light guide which will be discussed later, in order to form the wavelength converting member.

Mode Scrambler

The light emitting device of the present invention may be equipped with a mode scrambler.

The mode scrambler changes the radiation pattern of the excited light introduced to the light guide to a different radiation pattern (light intensity pattern) and radiates excitation light from the light guide, and any device and any arrangement which can accomplish this function is acceptable. In other words, with regards to the excitation light introduced to the light guide, any device is acceptable which can show a different radiation pattern when excitation light which is mode scrambled and radiated from a light guide is compared to excitation light which is not mode scrambled and radiated from the light guide. For instance, in the field of optical communication, a device may be exemplified which uses a commonly known method for easily measuring the optic fiber connection losses or the like or for converting the radiation pattern of light introduced to an optic fiber.

Specifically, the mode scrambler can be made of a member which has a concave region and/or a convex region facing a part or all of the outer circumference and a part or all of the longitudinal direction of the light guide. In other words, the mode scrambler can be formed by a member which can bend the light guide in multiple directions by contacting the light guide in the concave region and/or the convex region or pressing on the concave and/or convex region. Herein, multiple directions refers to any direction in two directions or three or more directions in a two-dimensional or three-dimensional system.

Figure 5:
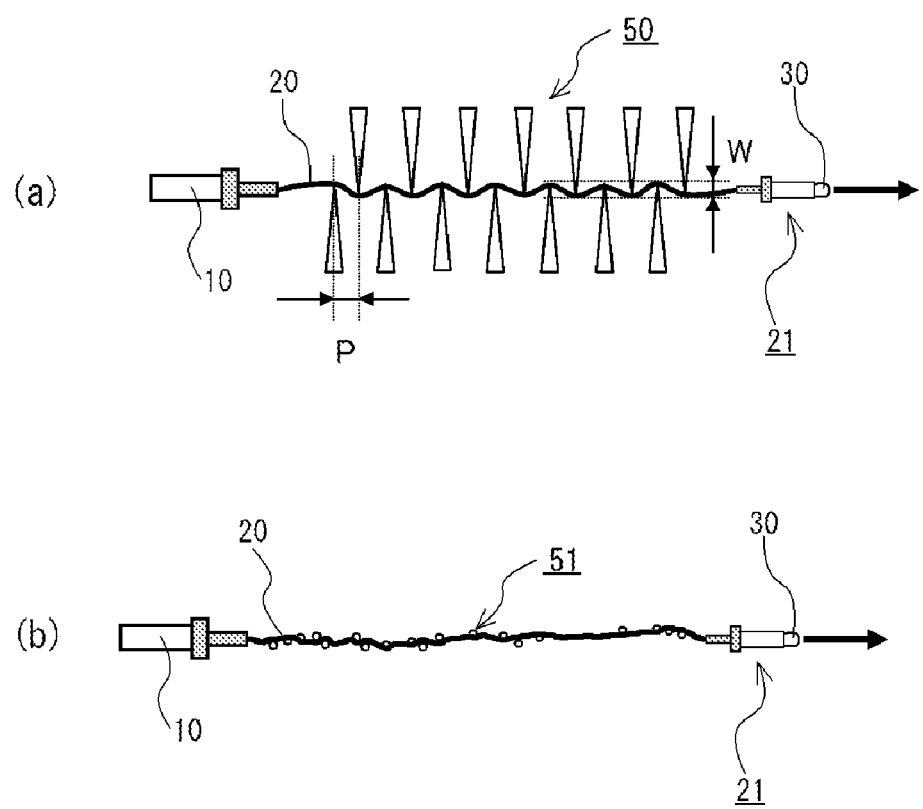
FIGS. 5(a) and 5(b) are schematic diagrams for describing the structure of the mode scrambler of the light emitting device of the present invention.
Figure 6:
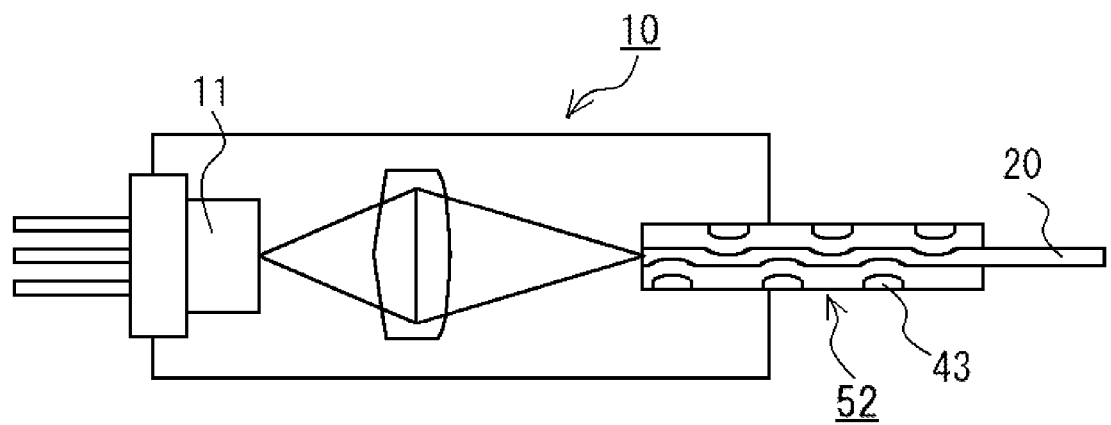
FIG. 6 is a schematic diagram for describing the construction of another mode scrambler for the light emitting device of the present invention.

For instance, as shown in FIG. 5(a), a mode scrambler 50 has pectinate concave and convex forms which mate in order to two-dimensionally bend the light guide in two directions like a wave. Furthermore, as shown in FIG. 5(b), a mode scrambler 51 is presented which has granular, convex, or concave shapes or the like in order to be able to three-dimensionally bend the light guide in multiple directions in an arbitrary distribution. Furthermore, as shown in FIG. 6, the light guide 20 may be warped by partially fusing (by YAG welding or the like) the side surface of a ferrule or the like (made from SUS or nickel or the like) (43 in FIG. 4) which has been attached along a part or all of the light guide 20, resulting in a method and/or a member which can bend the light guide in multiple directions. In other words, a member which can bend the light guide itself or the light guide core using outside forces can be exemplified.

The bending may be orderly or randomly distributed, but is preferably performed in multiple directions in a gradual rounded smooth shape in order to prevent damaging the light guide. In other words, the radius of the curvature may be 1 mm or larger, and preferably between approximately 10 and 100 mm.

The bending may be distributed along the whole length of the light guide, but may also be concentrated near the excitation light source side, the wavelength converting member side, or the middle area.

The bending is preferably performed in two or more locations, more preferably in 4 or more locations, 6 or more locations, 8 or more locations, 10 or more locations, 15 or more locations, 20 or more locations, and 40 or more locations of the light guide. The bending pitch (P in FIG. 5(a)) and the bending width (W in FIG. 5(a)) of the bending is not restricted in particular, but for instance, the bending pitch is preferably 100 mm or less, and more preferably 50 mm or less, 10 mm or less, 5 mm or less, or 1 mm or less. The bending width for instance is preferably 10 mm or less, 8 mm or less, 6 mm or less, 5 mm or less, 3 mm or less, 1 mm or less, and preferably 0.05 mm or higher, 0.1 mm or higher, and 0.3 mm or higher. Note that the bending pitch and bending width of the bending may be the same size throughout or may have various sizes.

Figure 7:
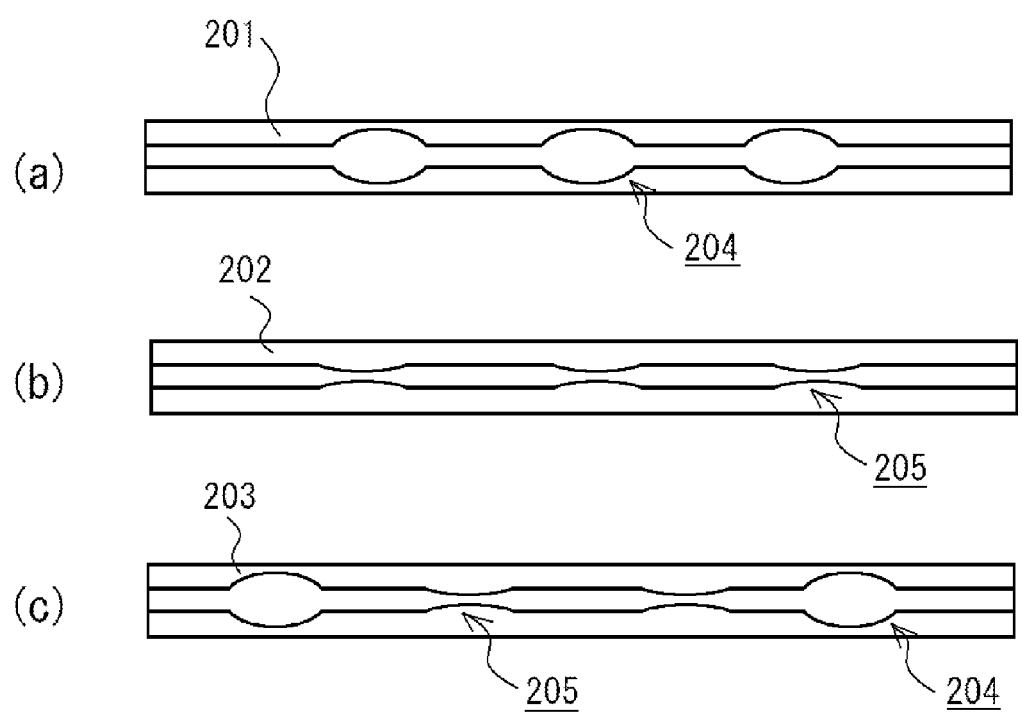
FIGS. 7(a) to 7(c) are schematic diagrams for describing the structure of yet another mode scrambler for the light emitting device of the present invention.

Furthermore, the mode scrambler may also be a member which is integrated into the light guide and changes the diameter of the middle region by increasing and decreasing the thickness of the outer circumference of the light guide. In other words, a part of the light guide clad may also function as the mode scrambler. For instance, as shown in FIG. 7(a) to (c), TEC processing or the like may be performed in predetermined regions of the light guide 201, 202, 203 so that part of the core has areas with increased diameter (204 in FIG. 7(a)), areas with increased diameter (205 in FIG. 7(b)), and areas with increased and decreased diameter (204 and 205 in FIG. 5(c)).

Note that in this case, the distribution and condition of the changes in the diameter of the center region (core) as well as the number and pitch thereof are the same as described above. The changes in the diameter of the center region are preferably 4/5 of the diameter or less, and more preferably 1/2 or less, 40% or less, 35% or less, 30% or less, or 20% or less.

By using this type of mode scrambler, the excitation light introduced to the light guide can be mode scrambled in order to obtain the desired radiation beam. For instance, the excitation light after mode scrambling preferably has a full width at half maximum FFP that is 1.5 times or higher, and more preferably 1.8 times or higher, 2 times or higher, 2.2 times or higher, or 2.5 times or higher than the excitation light before mode scrambling. In other words, the excitation light introduced to the light guide is mode scrambled, and the full width at half maximum of the FFP of the excitation light radiated from the light guide is preferably 1.5 times or higher and more preferably 1.8 times or higher, 2 times or higher, 2.2 times or higher, or 2.5 times or higher than the full width at half maximum FFP of the excitation light radiated from the light guide without being mode scrambled. Therefore the light density concentration to extremely narrow locations can be relieved while maintaining high brightness, degradation due to heating of the wavelength converting member can be prevented, thus contributing to longer life for the light emitting device. Herein, full width at half maximum is also referred to as FWHM, and normally refers to the full width of the intensity at half of the value of the intensity peak for response curves with regards to the width of the intensity of a radiation beam. The profile of the radiation beam may use any method and device commonly known in this field, and for instance, commercial devices such as FTS-4000A (produced by Santec Corp.) and LEPAS-11 (produced by Hamamatsu Photonics) or the like may be used.

Furthermore, from another viewpoint, the mode scrambler preferably provides excitation light after mode scrambling which has an intensity peak at FFP that is 90% or less, and more preferably 80% or less, 75% or less, or 70% or less than that of the excitation light prior to mode scrambling. In other words, the excitation light which is introduced to the light guide is mode scrambled and the intensity peak value in the FFP of the excitation light radiated from the light guide is preferably 90% or less, and more preferably 80% or less, 75% or less, or 70% or less than the intensity peak value of the FFP of the excitation light radiated from the light guide without being mode scrambled. Therefore, there will be a slight drop in the intensity peak value, but only the change in the shape of the radiation beam required to compensate for the drop in the intensity peak value is performed, so for the overall light emitting device, the high brightness can be maintained while relieving light density concentrations in extremely small regions.

Lens

With the light emitting device of the present invention, a lens 13 may also be established between the laser elements 11 and the radiating part 12, as shown in FIG. 1 for instance.

The lens may have any configuration so long as the light radiated from the laser element is collected to the incidence region of the light guide, and a plurality of lenses may be arranged in a line between the laser element and the radiating part. The lens may be formed from inorganic glass or plastic or the like, but of these inorganic glass is preferable. The excitation light radiated from the excitation light source can be collected and efficiently guided to the light guide by providing a lens between the excitation light source and the light guide such that the excitation light radiated from the excitation light source can be guided through the lens to the light guide.

Note that the lens may contain material which acts as a wavelength converting member for the fluorescent material. Thereby the wavelength converted excitation light can positively be collected to the radiating part by the lens function and therefore color variation can be eliminated and the cost of manufacturing the wavelength converting member can be held down because the wavelength converting member can be simultaneously manufactured by manufacturing the lens.

Light Guide End Member

With the light emitting device of the present invention, the end of any one of the 1st to 3rd light guides, or in other words the end which is not connected to the excitation light source, is preferably supported by a light guide end member normally called a ferrule. The radiating light from the light guide can easily be fixed by this light guide end member. Furthermore, depending on the material and shape thereof, the light emitting efficiency can be increased and the assembly of the light emitting device can be simplified.

Therefore, the light guide end member may be constructed using any material and configuration so long as the light guide can be supported.

The light guide end member is preferably formed from a material which has high reflectivity towards the wavelength converted light and/or the excitation light, high refractive index for light, or high thermal conductivity, or a material which provides two or more of these characteristics. For instance, materials which have reflectivity of 80% or higher towards the wavelength converted light and/or the excitation light, a refractive index of n:1.4 or higher towards 300 to 500 nm light, and/or a thermal conductivity of 0.1 W/m° C. or higher are preferable. Specific examples include Ag, Al, $ZrO_2$, boron silicate glass, stainless steel (SUS), carbon, copper, and barium sulfate or the like. Of these materials, $ZrO_2$ has high reflectivity and can easily be processed so that the light guide can pass through, and stainless steel can easily maintain high tensile strength, so forming the end member from $ZrO_2$ or stainless steel (for instance SUS 303 or the like) is preferable.

The light guide end member may for instance have a cylindrical shape in order to cover the outer circumference of the light guide, and various functional films or members which provide various functions to the end surface of the light guide may be integrated with or attached separately thereto, or a cover or cap or the like which covers the end surface of the light guide as well as other functional films or members or the like may be integrated with or separately attached thereto. Note that if the light guide end member has a cylindrical configuration, the diameter is for instance preferably 3 mm or less.

Functional Membranes and Members

Even if the aforementioned light guide end member is not attached, the light emitting device of the present invention preferably has various functional films or members attached in appropriate locations. Examples of these functional films and members include for instance a wavelength converted light reflecting film, excitation light reflecting film, scatter preventing member, and scattering member or the like.

The wavelength converted light reflecting film prevents wavelength converted light from the wavelength converting member from returning to the excitation light incidence side and also can be used to externally discharge by reflecting light which has returned to the excitation light incidence side. Therefore, the wavelength converted light reflecting film is preferably formed from a material which can transmit only certain wavelengths of light while reflecting certain wavelengths, or in other words, wavelength converted light. Thereby the light which returns to the excitation light incidence side can be reflected and the light emitting efficiency can be increased. Furthermore, the wavelength converted light reflecting film is preferably located at least on the excitation light incidence region of the wavelength converting member.

The excitation light reflecting film can be used to prevent the excitation light from radiating directly to the outside or to prevent the excitation light from leaking to unintended areas. Thereby, excitation light which has passed through the wavelength converting member but was not wavelength converted by the fluorescent material or the like can be returned back to the wavelength converting member in order to increase the light emitting efficiency. Therefore, the excitation light reflecting film is preferably formed from a material which allows transmission of only light of a specific wavelength which has been wavelength converted but reflects excitation light. Furthermore, the excitation light reflecting film is preferably located at least on the wavelength converted light emission region of the wavelength converting member. Thereby radiation of excitation light to the outside can be reduced and the light emitting efficiency can be increased.

The scatter preventing member can be used to prevent excitation light and/or wavelength converted light from scattering in unintended directions. Therefore, the scatter preventing member is preferably constructed with materials and shape which block 90% or more of the excitation light or the wavelength converted light. For instance, at the joint between the light guide and the wavelength converting member, the scatter preventing member may placed between the light guide and the wavelength converting member, or may be placed to surround the boundary region between the light guide and the wavelength converting member, or may be placed to cover the outside surface of the wavelength converting member except for the wavelength converted light emitting region.

The scattering member can be used to increase the light emitting efficiency by causing more of the excitation light to shine on the fluorescent material or the light of the wavelength converting member primarily by scattering the excitation light. Therefore the scattering member is preferably placed between the light radiating port of the light guide and the wavelength converting member. The scattering member may be made from the aforementioned resins which have relatively high refractive index or the aforementioned resins with the aforementioned fillers for instance. Of these materials, a silicone resin is preferable. Thereby the output of light which shines on the wavelength converting member can be reduced and the load on the wavelength converting member per unit area can be reduced in order to increase light emitting efficiency and linearity.

For instance, the film thickness of the scattering member can be appropriately adjusted depending on the core diameter of the light guide, the refractive index and thickness of the optional scattering member, and the size of the wavelength converting member or the like.

Shielding Member

The light emitting device of the present invention may also have a shielding member attached. The shielding member preferably shields 90% or more of the light from the excitation light source. Thereby only light of specific wavelengths may pass through. For instance, when using a light emitting element which radiates ultraviolet light which is harmful to humans, an ultraviolet light absorbing agent or reflecting agent or the like may be added to the wavelength converting member in the light emitting region as a shielding member for shielding the ultraviolet rays. Therefore, emission of ultraviolet rays or the light can be suppressed. Using a reflecting agent is preferable over an absorbing agent from the viewpoint that the light emitting efficiency can be further increased.

Note that the shielding member may also function as the aforementioned excitation light reflecting film or the scatter preventing film or the like so these materials may be used without strictly distinguishing.

Light Emitting Device Applications

The light emitting device of the present invention with can be used in a variety of applications. For instance, the device may be used as a normal lighting fixture or as automotive lighting (specifically a light source for headlamps and tail lamps or the like), or may be used as a device such as an endoscope for observing inside a living body and performing treatment during observation. Furthermore, the device may also be used as a fiber scope for observing inside extremely narrow or dark spaces such as inside an atomic reactor or inside the space of enclosed artifacts. The device may also be used as a light source for various industrial, construction, and residential applications in members where current leak and heating or the like are to be avoided such as in the chamber of various vacuum devices. In addition, the device may be used as a light emitting device for use in regions where a light source is required or where replacing a light source is difficult.

Therefore, this light emitting device can be used together with an imaging member (in other words an electronic component which converts an optical image to electronic signal (photoreceptor element)), specifically with an imaging element which uses a CCD (charge coupled device) or CMOS (CMOS image sensor), as well as with an image signal processing device which converts an electric signal to an image signal, an indicator for displaying the electronic signal or a measurement value or the like, a display which outputs an image signal and creates an image, and a computer which performs various processes and calculations. In particular, when using an imaging element as an imaging member, the optical image of the object being photographed can easily be handled.

For instance, a photoreceptor element (such as a photo diode or the like) may be established separate from the light emitting device, but may also be established in the light guide end member or around the light guide in close proximity to the laser elements in the excitation light source. Thereby the intensity of light generated from the laser elements can be measured by the photoreceptor element, and when the intensity of light is below a fixed level, the current supplied to the laser element can be adjusted in order to maintain a fixed intensity of light.

The light emitting device of the present invention has high brightness with minimal color variation, extremely good color reproduction, and excellence color rendering properties, and therefore displays excellent effects for use in devices which require brilliant images or the like such as endoscope devices.

Furthermore, the light emitting device of the present invention can also be used for visible light communication. In other words, a wireless environment can be created by using visible light obtained from the aforementioned light emitting device and adding communication functions to the light emitting device. Thereby modulation speeds of several hundred MHz can be achieved because a laser element is used as the excitation light source.

Furthermore, the light emitting device of the present invention can be used as an image display device which displays a color image on an image display unit (screen). The light emitting device of the present invention can generate extremely bright light at high light emitting efficiencies, and can therefore show excellent effects as a light source for end image display devices.

Next an embodiment of the light emitting device of the present invention will be described in detail based on the drawings.

Embodiment 1

As shown in FIG. 1, the light emitting device of this embodiment is constructed by combining two units each comprising an excitation light source 10, a light guide 20, and a wavelength converting member 30.

The first unit uses a blue laser element 11 with a GaN semiconductor which has an emission peak wavelength around 445 nm as the excitation light source 10. A lens 13 for collecting the excitation light 1 from the laser element is located in front of the laser element.

The light guide 20 is connected on one end to the light radiating part 12 of the excitation light source 10, and connected on the other end to the output unit 21. The light guide 20 is made from quartz and for instance has Si 114 (μm: core diameter)/125 (μm: clad diameter).

The wavelength converting member 30 was molded to uniformly disperse the fluorescent material throughout the resin, and is attached to the output unit 21.

The fluorescent material was made by mixing 0.54 g of $(Lu, Ce)_3Al_5O_{12}$:Ce (LAG) which emits green light with 0.02 g of $(Ca, Sr)_2Si_5N_8$:Eu (SCESN) which emits red light as the fluorescent material in 1.1 g of silicone resin. The film thickness of the wavelength converting material 30 in this case was approximately 500 μm.

The second unit used a laser element comprising a GaN semiconductor which had an emission peak wavelength around 405 nm as the excitation light source. A lens for collecting the excitation light from the laser element was positioned in front of the laser element.

The light guide was as described above.

The wavelength converting member was molded in order to uniformly disperse the fluorescent material throughout the resin, and was attached to the output unit.

The fluorescent material was made by mixing 0.42 g of $Ca_{10}(PO_4)_6Cl_2$:Eu (CCA) which emits blue light with 0.54 g of $(Lu, Ce)_3A_5O_{12}$; Ce (LAG) which emits green light and 0.02 g of $(Ca, Sr)_2Si_5N_8$:Eu (SCESN) which emits red light as the fluorescent material in 1.1 g of silicone resin. The film thickness of the wavelength converting material 30 was approximately 500 μm.

Figure 8:
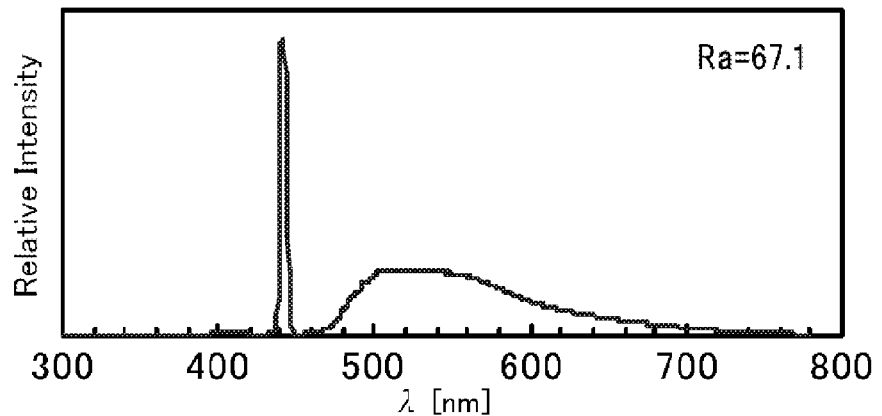
FIG. 8(a) to (c) are diagrams showing the light emitting spectrum of a laser element for the light emitting device of the first embodiment.
Figure 8:
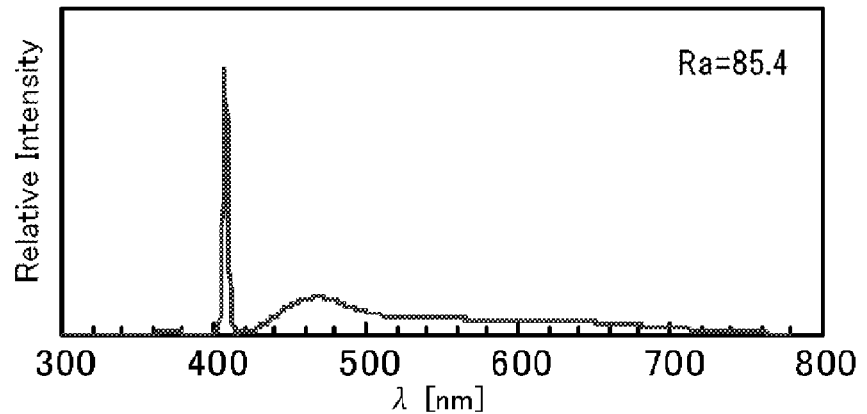
Figure 8:
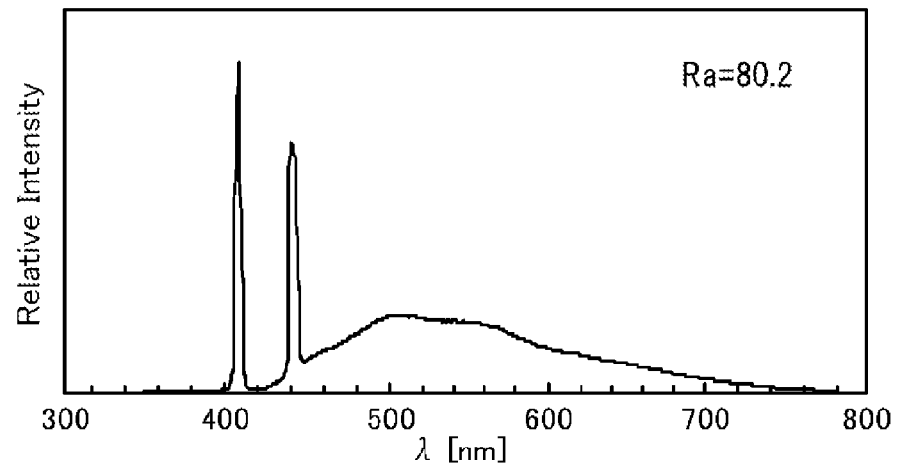
Figure 9:
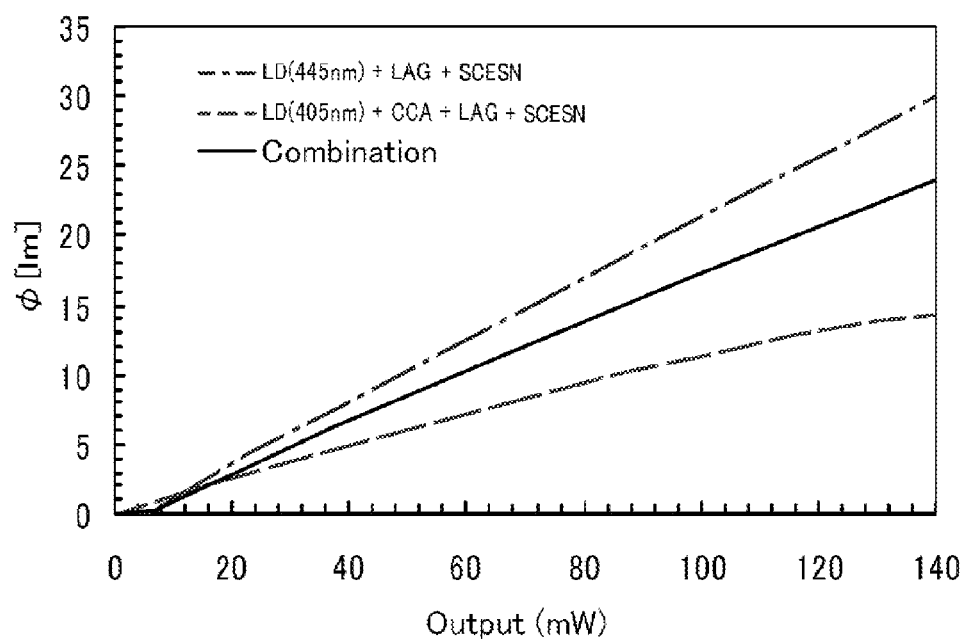
FIG. 9 is a graph showing the light emitting efficiency for the light emitting device of the first embodiment.

The first and second unit have a linear spectrum in each of the excitation wavelengths and extremely low intensity around this wavelength band when each of the excitation light sources are driven with 50 mW, as shown in FIGS. 8(a) and (b) respectively. Furthermore, the first unit has relatively poor color rendering properties of Ra=67.1, but has extremely high light emitting efficiency as shown by the single point broken line of FIG. 9. The second unit as relatively good color rendering properties of Ra=85.4, but has poor linearity and shows relatively poor light emitting efficiency as shown by the broken line in FIG. 9.

On the other hand, by combining one unit of each of the first and second units in the light emitting device of the present invention, light 2 which has the light emitting spectrum shown in FIG. 8(c) can be obtained. This light 2 has a white color, and has a good average color rendering evaluation value (Ra) of 80.2. Furthermore, with regards to the light emitting efficiency, as shown by the solid line in FIG. 9, light could be obtained which had high brightness and good linearity.

Therefore a light emitting device can be obtained which radiates light with good color rendering properties, very minimal color variation, and good color reproduction with high brightness.

Embodiment 2

A light emitting device of this embodiment was produced essentially identical to the device of the first embodiment except that SCESN was replaced with SESN in both the first and second units.

When evaluated similar to the first embodiment, essentially the same results for color rendering properties and light emitting efficiency were obtained.

Embodiment 3

Figure 10:
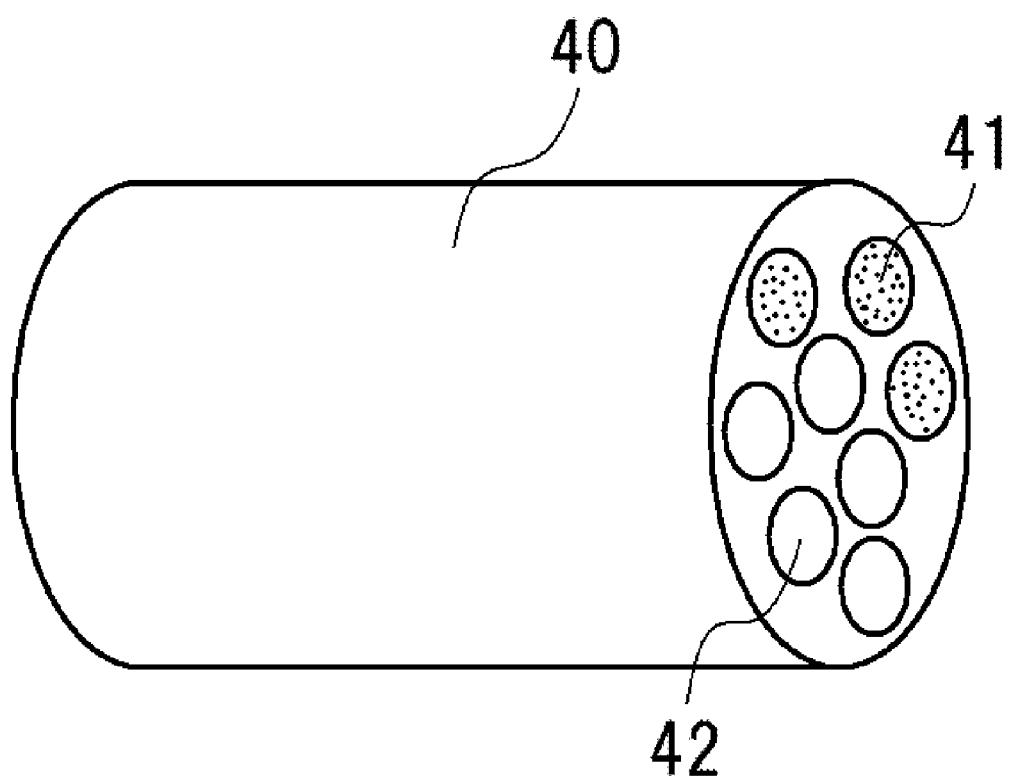
FIG. 10 is a schematic diagram for describing the combination structure for units of the light emitting device of the present invention.

As shown in FIG. 10, a light source device with high color rendering properties of Ra=80, good linearity and high light emitting efficiency could be obtained using this light emitting device by combining five of the first units 42 (excitation wavelength 445 nm) obtained in the first embodiment and three of the second units 41 (excitation wavelength 405 nm) using a bundle fiber 40.

Embodiment 4

This light emitting device was produced similar to the light emitting device of the third embodiment except that after combining five of the first units 42 (excitation wavelength 445 nm) and three of the second units 41 (excitation wavelength 405 nm) using a bundle fiber 40, the wavelength converting member used for the first unit of the first embodiment was integrated with the five first units and the wavelength converting member used for the second unit was integrated with the three second units. Similar to the third embodiment, the results confirmed that a light source device which had high color rendering properties and good light emitting efficiency could be obtained.

Embodiment 5

As shown in FIG. 1, the light emitting device of this embodiment comprises an excitation light source 10, a light guide 20, a mode scrambler (not shown in the figures) and a wavelength converting member 30.

The excitation light source 10 used a laser diode as a semiconductor light emitting element 11 which has an emission peak wavelength around 405 nm. The laser diode was a GaN type semiconductor element.

The light guide 20 was connected on one end to the light radiating part 12 of the excitation light source 10, and connected on the other end to the output unit 21. The light guide 20 was made from quartz and for instance was Si 114 (μm: core diameter)/125 (μm: clad diameter).

Figure 11:
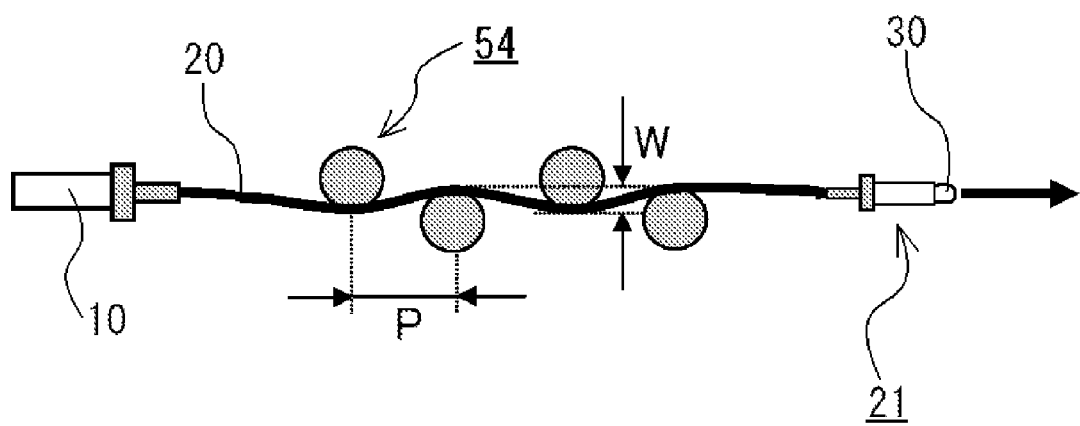
FIG. 11 is a schematic diagram showing the light emitting device of the fifth embodiment.

As shown in FIG. 11, the mode scrambler 54 was a comb-like member which periodically mated to the light guide 20 in 4 μredetermined locations to provide bends with a bending pitch P of 5 mm and a bending width W of 0.5 mm.

The wavelength converting member 30 was molded in order to uniformly disperse the fluorescent material throughout the resin, and was attached to the output unit 21.

The fluorescent material was made by mixing 0.54 g of $(Lu, Ce)_3Al_5O_{12}:Ce$ (LAG) which emits green light with 0.02 g of $(Ca, Sr)_2Si_5N_8:Eu$ (SCESN) which emits red light as the fluorescent material in 1.1 g of silicone resin. The film thickness of the wavelength converting material 30 in this case was approximately 500 μm.

In the excitation light source 10, a lens 13 for collecting the excitation light 1 from the laser diode was located in front of the semiconductor light emitting element 11.

Figure 12:
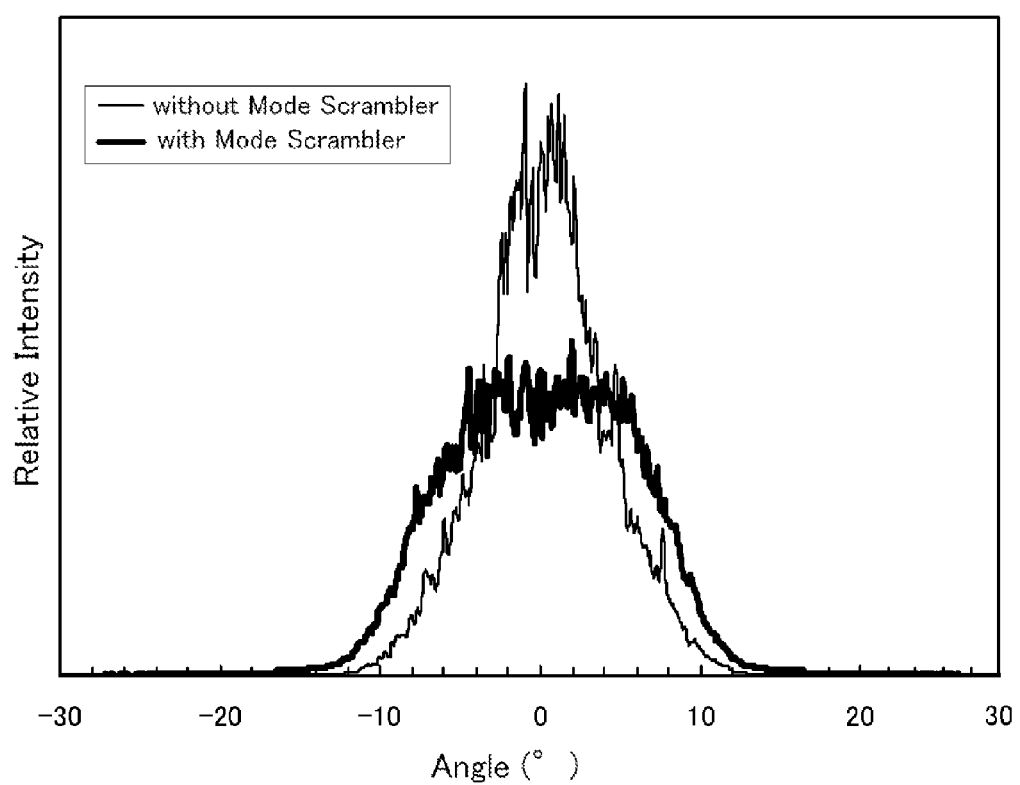
FIG. 12 is a graph showing the radiation pattern profile for the light emitting device of the fifth embodiment.

With this light emitting device, a radiation beam profile as shown by the bold line in FIG. 12 was obtained when the excitation light source was driven with 100 mW.

Note that a light emitting device identical to the aforementioned light emitting device except without the mode scrambler 52 was prepared for comparison, and when similarly driven with 100 mW, the radiation beam profile as shown by the fine line in FIG. 12 was obtained.

The comparison light emitting device had a half value width of 6.2°, and if the intensity peak was considered to be 100%, the value of the intensity peak of the light emitting device of the present embodiment was 56.7%. Furthermore, the half value width of the present embodiment was 15.2°, or approximately 2.3 times.

Figure 13:
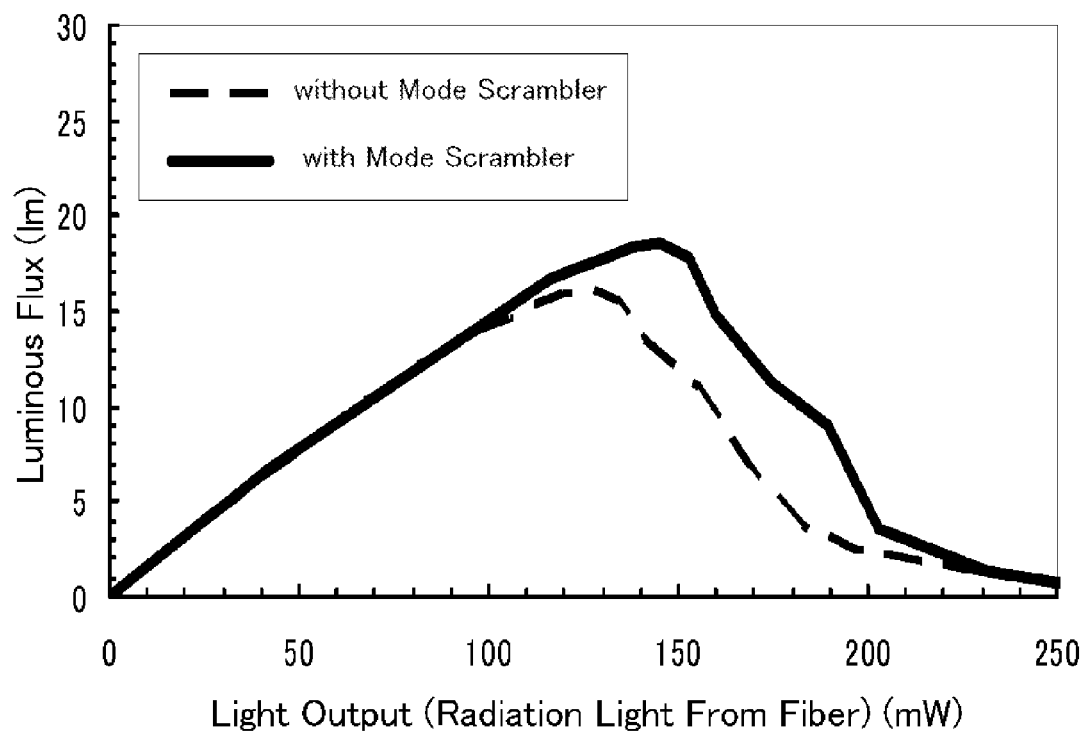
FIG. 13 is a graph showing the relationship between luminous flux and light output for the light emitting device of the fifth embodiment.

When the relationship between the luminous flux to light output was measured for both devices, as shown by the bold line in FIG. 13, the light emitting device of the present embodiment showed much better linearity than the light emitting device for comparison (broken line in FIG. 13).

Furthermore, the light emitting device of the present embodiment had good color rendering properties and when compared to the light emitting device for comparison, degradation of the wavelength converting member or the like was not observed whatsoever over a considerably long period of time, and thus longer life was confirmed.

Embodiment 6

The light emitting device of this embodiment is essentially the same device as the device of the first embodiment except that 20 beads of approximately 4 mm in size were randomly positioned on the outer circumference of the light guide 20 as a mode scrambler 51 in order to bend the light guide 20 as shown in FIG. 5(b).

When evaluated similar to the first embodiment, the results showed that the radiation beam profile, luminous flux to light output, and device life were nearly similar.

Embodiment 7

As shown in FIG. 6, this light emitting device was essentially the same device as the device of the first embodiment except that an SUS ferrule was welded as a mode scrambler 52 to create a force in six locations.

When evaluated similar to the first embodiment, the results showed that the radiation beam profile, luminous flux to light output, and device life were nearly similar.

Embodiment 8

As shown in FIG. 3(a), this light emitting device was essentially the same device as the device of the first embodiment except that the core diameter of the light guide was widened (1.5 times the middle core diameter) only at the end where the wavelength converting member 30 was positioned.

When evaluated similar to the first embodiment, the results showed that the radiation beam profile, luminous flux to light output, and device life were nearly similar.

This application claims priority to Japanese Patent Application No. 2004-363103 and 2004-366646. The entire disclosure of Japanese Patent Application No. 2004-363103 and 2004-366646 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A light emitting device comprising a first unit and a second unit, the first unit comprising:
    a first excitation light source comprising a laser element emitting blue wavelength band excitation light;
    a first wavelength converting member comprising at least one type of fluorescent material and which absorbs at least a portion of a first excitation light emitted from the first excitation light source, converts the wavelength, and releases light with a wavelength longer than the first excitation light; and
    a first light guide which has a refractive index in the center region of the cross-section which is higher than the refractive index of a surrounding region and which transmits the first excitation light emitted from the first excitation light source;
    and the second unit comprising:
    a second excitation light source comprising a laser element which emits excitation light with a wavelength band shorter than the blue wavelength band excitation light emitted by the laser element of the first excitation light source;
    a second wavelength converting member which includes at least one type of fluorescent material and which absorbs at least a portion of a second excitation light emitted from the second excitation light source, converts the wavelength, and releases light with a wavelength longer than the second excitation light; and
    a second light guide which has a refractive index in the center region of the cross-section which is higher than the refractive index of a surrounding region and which transmits the second excitation light emitted from the second excitation light source.

2. The light emitting device according to claim 1, wherein the first excitation light source contains a laser element which emits excitation light with a wavelength in the range of 430 to 500 nm.

3. The light emitting device according to claim 1, wherein the second excitation light source contains a laser element which emits excitation light with a wavelength in the range of 360 to 420 nm.

4. The light emitting device according to claim 1, wherein the first and/or the second wavelength converting member comprises fluorescent material and resin, and the fluorescent material and resin are mixed at a weight ratio of 0.1 to 10:1.

5. The light emitting device according to claim 1, wherein the fluorescent material of the first unit is a combination of rare earth aluminate and oxynitride or nitride.

6. The light emitting device according to claim 1, wherein the fluorescent material of the second unit is a combination of rare earth aluminate and alkali earth metal halogen apatite, or a combination of rare earth aluminate and alkali earth metal halogen apatite and oxynitride or nitride.

7. The light emitting device according to claim 1, further comprising a lens between the first excitation light source and the first light guide or between the second excitation light source and the second light guide, and wherein the excitation light emitted from the excitation light source is introduced to the light guide through the lens.

8. The light emitting device according to claim 1, wherein light radiated from the light emitting device has an average color rendering evaluation value (Ra) which is 70 or higher.

9. The light emitting device according to claim 1, further comprising a mode scrambler which applies mode scrambling to the first and/or second excitation light which is introduced to the first and/or second light guide.

10. A light emitting device comprising:
    an excitation light source which emits excitation light;
    a wavelength converting member which absorbs at least a part of the excitation light emitted from the excitation light source, converts the wavelength, and releases light with a predetermined wavelength band;
    a light guide with the excitation light source at one end and the wavelength converting member at the other end, and which has a refractive index in the center region of the cross-section which is higher than the refractive index of a surrounding region, and which transmits excitation light emitted from the excitation light source to the wavelength converting member; and
    a mode scrambler which applies mode scrambling to the excitation light which is introduced to the light guide.

11. The light emitting device according to claim 10, wherein the mode scrambler changes the radiation pattern of the excitation light introduced to the light guide to a different radiation pattern and causes this excitation light to be radiated from the light guide.

12. The light emitting device according to claim 10, wherein the mode scrambler bends the light guide in a plurality of directions.

13. The light emitting device according to claim 10, wherein the mode scrambler comprises a member which has concave regions and/or a complex regions facing a portion of or all of the outer circumference in a portion of or all of the longitudinal direction of the light guide.

14. The light emitting device according to claim 12, wherein the bending is performed in two or more locations either periodically or randomly.

15. The light emitting device according to claim 14, wherein the bending has a bending pitch which is 100 mm or less.

16. The light emitting device according to claim 14, wherein the bending has a bending width which is 10 mm or less.

17. The light emitting device according to claim 10, wherein the mode scrambler is integrated into the light guide, and changes the diameter of the center region by increasing and decreasing the thickness of the circumferential region of the light guide.

18. The light emitting device according to claim 17, wherein the change in the diameter of the center region is periodically or randomly performed in two or more locations.

19. The light emitting device according to claim 17, wherein the change in the diameter of the center region has a pitch which is 100 mm or less.

20. The light emitting device according to claim 17, wherein the change in the diameter of the center region is one half or less of the diameter.

21. The light emitting device according to claim 10, wherein the mode scrambler increases the full width half maximum of an FFP of the excitation light emitted from the light guide by two times or more.

22. The light emitting device according to claim 10, wherein the mode scrambler reduces the intensity peak value of an FFP of the excitation light emitted from the light guide to 80% or less.

23. The light emitting device according to claim 10, wherein the wavelength converting member contains fluorescent material and resin, and the fluorescent material and resin are mixed at a weight ratio of 0.1 to 10:1.

24. The light emitting device according to claim 10, wherein the fluorescent material contains at least one type of material selected from a group consisting of alkali earth metal halogen apatite, alkali earth metal aluminate, oxynitride or nitride, and rare earth aluminate.

25. The light emitting device according to claim 10, further comprising a lens between the excitation light source and the light guide, wherein the excitation light emitted from the excitation light source is introduced to the light guide through the lens.

26. The light emitting device according to claim 10, wherein light emitted from the light emitting device has an average color rendering evaluation value (Ra) which is 80 or higher.

* * * * *